United States Patent
Brunden et al.

(10) Patent No.: US 11,623,927 B2
(45) Date of Patent: Apr. 11, 2023

(54) SUBSTITUTED [1,2,4]TRIAZOLO[1,5-A]PYRIMIDINES FOR STABILIZING MICROTUBULES

(71) Applicants: THE TRUSTEES OF THE UNIVERSITY OF PENNSYLVANIA, Philadelphia, PA (US); THE REGENTS OF THE UNIVERSITY OF CALIFORNIA, Oakland, CA (US)

(72) Inventors: Kurt R. Brunden, Media, PA (US); Virginia M. Y. Lee, Philadelphia, PA (US); John Q. Trojanowski, Philadelphia, PA (US); Carlo Ballatore, San Diego, CA (US); Killian Oukoloff, San Diego, CA (US); Amos B. Smith, III, Merion, PA (US)

(73) Assignees: The Trustees of the University of Pennsylvania, Philadelphia, PA (US); The Regents of the University of California, Oakland, CA (US)

( * ) Notice: Subject to any disclaimer, the term of this patent is extended or adjusted under 35 U.S.C. 154(b) by 143 days.

(21) Appl. No.: 16/977,643

(22) PCT Filed: Feb. 28, 2019

(86) PCT No.: PCT/US2019/020014
§ 371 (c)(1),
(2) Date: Sep. 2, 2020

(87) PCT Pub. No.: WO2019/169111
PCT Pub. Date: Sep. 6, 2019

(65) Prior Publication Data
US 2020/0399269 A1  Dec. 24, 2020

Related U.S. Application Data

(60) Provisional application No. 62/637,486, filed on Mar. 2, 2018.

(51) Int. Cl.
| | | |
|---|---|---|
| A61K 31/519 | (2006.01) | |
| C07D 487/04 | (2006.01) | |
| C07D 471/04 | (2006.01) | |
| A61P 25/28 | (2006.01) | |
| C07D 519/00 | (2006.01) | |

(52) U.S. Cl.
CPC ............ C07D 471/04 (2013.01); A61P 25/28 (2018.01); C07D 519/00 (2013.01)

(58) Field of Classification Search
CPC ........................... A61K 31/519; C07D 487/04
USPC ...................... 514/262.1; 544/263
See application file for complete search history.

(56) References Cited

U.S. PATENT DOCUMENTS

| | | |
|---|---|---|
| 5,986,135 A | 11/1999 | Pfrengle et al. |
| 6,117,876 A | 9/2000 | Pees et al. |
| 7,524,849 B2 | 4/2009 | Zhang et al. |
| 9,649,317 B2 | 5/2017 | Ballatore et al. |
| 2003/0087888 A1 | 5/2003 | Regueiro-Ren et al. |

(Continued)

FOREIGN PATENT DOCUMENTS

| | | |
|---|---|---|
| WO | 2004/041824 A2 | 5/2004 |
| WO | 2005/030216 A1 | 4/2005 |

(Continued)

OTHER PUBLICATIONS

Aryla-Kaloustian et al, "Cevipabulin (TTI-237): preclinical and clinical results for a novel antimicrotubule agent.", Methods and Findings in Experimental and Clinical Pharmacology, vol. 31, No. 7, Sep. 2009, pp. 443-447.

(Continued)

*Primary Examiner* — Douglas M Willis
(74) *Attorney, Agent, or Firm* — BakerHostetler

(57) ABSTRACT

The present disclosure provides compounds of formula (I) or (II) or a pharmaceutically acceptable salt or stereoisomer thereof, wherein Rx-R8 are defined herein. Also provided are compositions comprising a compound described herein and a pharmaceutically effective excipient, methods of stabilizing microtubules in a patient comprising administering to the patient a microtubule-stabilizing amount of a compound described herein, methods of treating cancer in a patient comprising administering to the patient a therapeutically effective amount of a compound described herein, and methods of treating a neurodegenerative disease in a patient comprising administering to the patient a therapeutically effective amount of a compound described herein.

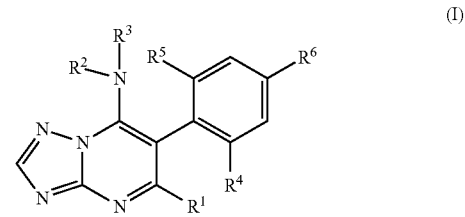

(I)

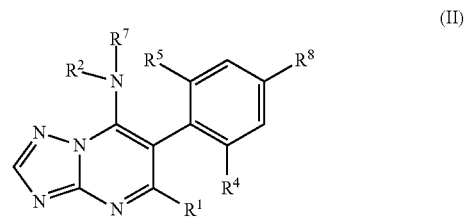

(II)

18 Claims, 1 Drawing Sheet

(56) References Cited

U.S. PATENT DOCUMENTS

| | | |
|---|---|---|
| 2005/0124635 A1 | 6/2005 | Wu et al. |
| 2012/0077810 A1 | 3/2012 | Chen et al. |
| 2014/0256747 A1 | 9/2014 | Zupancic et al. |
| 2014/0371449 A1 | 12/2014 | Maras et al. |
| 2015/0005498 A1 | 1/2015 | Zupancic et al. |
| 2015/0224105 A1 | 8/2015 | Ballatore et al. |
| 2016/0250358 A1 | 9/2016 | Marik et al. |
| 2016/0303150 A1 | 10/2016 | Megiddo |
| 2017/0173016 A1 | 6/2017 | Ballatore et al. |

FOREIGN PATENT DOCUMENTS

| | | |
|---|---|---|
| WO | 2005/030775 A1 | 4/2005 |
| WO | 2005/113555 A1 | 12/2005 |
| WO | 2005/117550 A2 | 12/2005 |
| WO | 2006/091728 A2 | 8/2006 |
| WO | 2006/138180 A1 | 12/2006 |
| WO | 2007/075465 A1 | 7/2007 |
| WO | 2008/084027 A1 | 7/2008 |
| WO | 2009/123486 A1 | 10/2009 |
| WO | 2011/037985 A1 | 3/2011 |
| WO | 2014/047257 A2 | 3/2014 |

OTHER PUBLICATIONS

Ballatore et al, "Discovery of Brain-Penetrant, Orally Bioavailable Aminothienopyridazine Inhibitors of Tau Aggregation", Journal of Medicinal Chemistry US, vol. 53, No. 9, May 13, 2010, pp. 3739-3747.

Ballatore et al, "Microtubule stabilizing agents as potential treatment for Alzheimer's disease and related neurodegenerative tauopathies.", Journal of Medicinal Chemistry, vol. 55, No. 21, Nov. 8, 2012, pp. 8979-8996.

Ballatore et al, "Tau-Mediated Neurodegeneration in Alzheimer's Disease and Related Disorders", Nature Reviews, Neuroscience, Sep. 2007, 8, 663-672.

Beyer et al, "TTI-237: A Novel Microtubule-Active Compound With In Vivo Antitumor Activity", Cancer Research, Apr. 1, 2008, 68, 2292-2300.

Black et al, "Dynamics of Alpha-Tubulin Deacetylation in Intact Neurons", Journal of Neuroscience, Jan. 1, 1989, 9(1), 358-368.

Brunden et al, "Brain-Penetrant Microtubule-Stabilizing Compounds as Potential Therapeutic Agents for Tauopathies", Biochem. Soc. Trans., 2012, 40, 661-666.

Brunden et al, "The Characterization of Microtubule-Stabilizing Drugs as Possible Therapeutic Agents for Alzheimer's Disease and Related Tauopathies", Pharmacological Research, Apr. 2011 63(4), 341-351.

Brunden et al., "Advances in tau-focused drug discovery for Alzheimer's disease and related tauopathies", Nature Reviews, Oct. 2009, vol. 8, 783-793.

Brunden et al., Epothilone D Improves Microtubule Density, Axonal Integrity and Cognition in a Transgenic Mouse Model of Tauopathy, Journal. Neuroscience, Oct. 13, 2010, 30(41), 13861-13866.

Buee et al, "Tau Protein Isoforms, Phosphorylation and Role in Neurodegenerative Disorders", Brain Research Reviews, Aug. 2000, 33(1), 95-130.

Cross et al., Brain Research 1618, 2015, 299-308.

Crowley et al. "Neimentowski-type Synthesis of Pyrido[3,2-e][1,2,4]Trazines: Potent Aza-Analogs of Pyrido[2,3-b]pyrazine Fungicides", Tetrahedron Letters, May 12, 2010, 51(19), 2652-2654.

Fanara et al., "Stabilization of Hyperdynamic Microtubules Is Neuroprotective in Amyotrophic Lateral Sclerosis," J. Bio. Chem, Aug. 10, 2007, vol. 282, No. 32, pp. 23465-23472.

Farah et al, "Altered Levels and Distribution of Microtubule-Associated Proteins Before Disease Onset in a Mouse Model of Amyotrophic Lateral Sclerosis", Journal of Neurochemistry, Jan. 2003, 84(1), 77-86.

Fellner et al., "Transport of paclitaxel (Taxol) across the blood-brain barrier in vitro and in vivo", The Journal of Clinical Investigation, Nov. 2002, vol. 110, No. 9,1309-1318.

International Application No. PCT/US2013/60562: International Search Report and the Written Opinion dated Apr. 10, 2014.

Johnson et al., "Axonal pathology in traumatic brain injury," Experimental Neurology 246, 1Jan. 20, 2012, pp. 35-43.

Kambe et al., "Mapping the Protein Interaction Landscape for Fully Functionalized Small-Molecule Probes in Human Cells," J. Am. Chem. Soc., 2014, 136 (30), pp. 10777-10782.

Laferriere et al, "Tubulin Synthesis and Assembly in Differentiating Neurons", Biochemistry and Cell Biology, Feb. 1997, 75(2), 103-117.

LaPlante et al., "Characterization of the Human Cytomegalovirus Protease as an Induced-Fit Serine Protease and the Implications to the Design of Mechanism-Based Inhibitors," J. Am. Chem. Soc., 1999, 121 (13), pp. 2974-2986.

Lee et al., Neurobiology, 1994, vol. 15, Suppl.2, pp. S87-S89.

Lei et al, "Tau Protein: Relevance to Parkinson's Disease", The International Journal of Biochemistry & Cell Biology, 42(11), Nov. 2010, 1775-1778.

Petratos et al, "Novel Therapeutic Targets for Axonal Degeneration in Multiple Sclerosis", Journal of Neuropathology, Experimental Neurology, Apr. 2010, 69(4), 323-334.

PubChem-CID 11655014, Create Date: Oct. 27, 2006, 3 pages, Https://pubchem.ncbi.nlm.nih.gov/summary/summary.cgi?cid= 11655014.

Rohena et al., "Recent progress with microtubule stabilizers: new compounds, binding modes and cellular activities", Natural Product Reports, 2014, 31, 335-355.

Roy et al, "Axonal Transport Defects: A Common Theme in Neurodegenerative Diseases", Acta Neuropathology, (Berl), Jan. 12, 2005, 109(1), 5-13.

Schmidt et al, "Tau Isoform Profile and Phosphorylation State in Dementia Pugilistica Recapitulate Alzheimer's Disease", Acta Neuropathology, Mar. 2001, 101, 518-524.

Shively et al, "Dementia Resulting From Traumatic Brain Injury", Arch Neurology., Jul. 9, 2012, 69(10), 1245-1251.

Smith et al, "Protein Accumulation in Traumatic Brain Injury", NeuroMolecular Medicine, Oct. 2003, 4(1), 59-72.

Tang-Schomer et al., "Mechanical breaking of microtubules in axons during dynamic stretch injury underlies delayed elasticity, microtubule disassembly, and axon degeneration," The FASEB Journal, Aug. 2016, vol. 24, No. 5, pp. 1401-1410.

Yoshiyama, "Enhanced Neurofibrillary Tangle Formation, Cerebral Atrophy, and Cognitive Deficits Induced by Repetitive Mild Brain Injury in a Transgenic Tauopathy Mouse Model", Journal of Neurotrauma, Oct. 2005, 22(10), 1134-1141.

Zhang et al. "The Microtubule-Stabilizing Agent, Epothilone D, Reduces Axonal Dysfunction, Cognitive Deficits, Neurotoxicity and Alzheimer-Like Pathology in an Interventional Study With Aged Tau Transgenic Mice", Mar. 14, 2012, The Journal of. Neuroscience, 32(11), 3601-3611.

Zhang, et al. "Microtubule-Binding Drugs Offset Tau Sequestration by Stabilizing Microtubules and Reversing Fast Axonal Transport Deficits in a Tauopathy Model", Proc. National Academy of Sciences USA, Jan. 4, 2005,102(1), 227-231.

Ballatore et al., Non-Naturally Occurring Small Molecule Microtubule-Stabilizing Agents: A Potential Tactic for CNS-Directed Therapies. ACS Chem Neurosci. 2017, 8, 5-7.

Beyer et al., The microtubule-active antitumor compound TTI-237 has both paclitaxel-like and vincristine-like properties. Cancer Chemother. Pharmacol. 2009, 64, 681-9.

Cornec et al., Pharmacokinetic, pharmacodynamic and metabolic characterization of a brain retentive microtubule (MT)-stabilizing triazolopyrimidine. Bioorg. Med. Chem. Lett. 2015, 25, 4980-2.

Crowley et al., Synthesis and fungicidal activity of tubulin polymerisation promoters. Part 1: pyrido[2,3-b]pyrazines. Pest. Manag. Sci. 2010, 66, 178-185.

Dean et al., Review of deutetrabenazine: a novel treatment for chorea associated with Huntington's disease, Drug Des Devel. Ther., Feb. 15, 2018.

(56) References Cited

OTHER PUBLICATIONS

Fukushima et al., Post-translational modifications of tubulin in the nervous system. J Neurochem 2009, 109.

Kovalevich et al., Characterization of brain-penetrant pyrimidine-containing molecules with differential microtubule-stabilizing activities developed as potential therapeutic agents for Alzheimer's disease and related tauopathies. J. Pharmacol. Exp. Ther. 2016, 357, 432-50.

Lamberth et al., Synthesis and fungicidal activity of tubulin polymerisation promoters. Part 2: Pyridazines. Bioorg. Med. Chem. 2012, 20, 2803-10.

Lamberth et al., Synthesis and fungicidal activity of tubulin polymerisation promoters. Part 3: imidazoles. Bioorg Med Chem 2013, 21, 127-34.

Lou et al., Brain-penetrant, orally bioavailable microtubule-stabilizing small molecules are potential candidate therapeutics for Alzheimer's disease and related tauopathies J. Med. Chem. 2014, 57, 6116-27.

Oukoloff et al., Design, synthesis and evaluation of photoactivatable derivatives of microtubule (MT)-active [1,2,4]triazolo[1,5-a]pyrimidines, Bioorganic & Medicinal Chemistry Letters 28 (2018) 2180-2183.

Pirali et al., Applications of Deuterium in Medicinal Chemistry, J Med Chem, Jun. 13, 2019; 62(11): 5276-5297, Epub: Jan. 25, 2019.

Robinette et al., Photoaffinity labeling combined with mass spectrometric approaches as a tool for structural proteomics. Expert Rev Proteomics 2006, 3, 399-408.

Sáez-Calvo et al., Triazolopyrimidines Are Microtubule-Stabilizing Agents that Bind the Vinca Inhibitor Site of Tubulin. Cell Chemical Biology 2017, 24, 737-750 e6.

Schmidt, First deuterated drug approved, Nature Biotechnology, May 31, 2017, 35(6): 493-494.

Zhang et al., 2-cyanoaminopyrimidines as a class of antitumor agents that promote tubulin polymerization. Bioorg. Med. Chem. Lett. 2007, 17, 3003-5.

Zhang et al., A brain-penetrant triazolopyrimidine enhances microtubule-stability, reduces axonal dysfunction and decreases tau pathology in a mouse tauopathy model, Mol. Neurodegener., Nov. 7, 2018, 13(1):59.

Zhang et al., Synthesis and SAR of [1,2,4]triazolo[1,5-a]pyrimidines, a class of anticancer agents with a unique mechanism of tubulin inhibition. J. Med. Chem. 2007, 50, 319-27.

Zhang et al., Synthesis and SAR of 6-chloro-4-fluoroalkylamino-2-heteroaryl-5-(substituted)phenylpyrimidines as anti-cancer agents. Bioorg. Med. Chem. 2009, 17, 111-8.

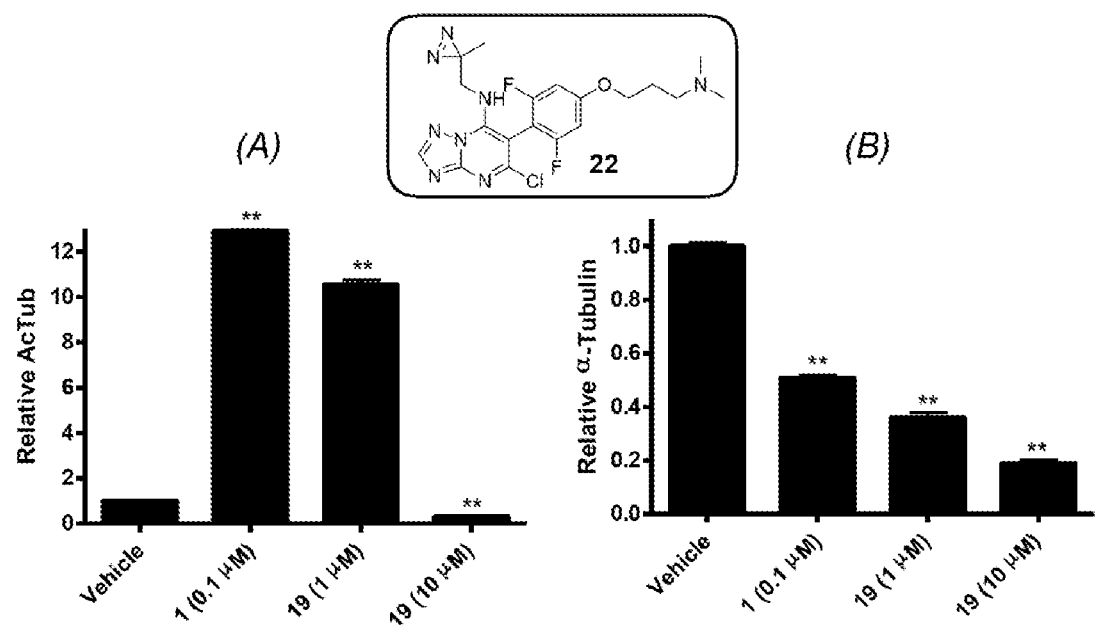

SUBSTITUTED [1,2,4]TRIAZOLO[1,5-A]PYRIMIDINES FOR STABILIZING MICROTUBULES

CROSS-REFERENCE TO RELATED APPLICATIONS

This application is the National Stage Application of International Patent Application No. PCT/US2019/020014, filed Feb. 28, 2019, which claims the benefit of U.S. Provisional Patent Application No. 62/637,486, filed Mar. 2, 2018, both of which are incorporated by reference herein.

GOVERNMENT RIGHTS

This invention was made with government support under grant number AG044332 awarded by the National Institutes of Health. The government has certain rights in the invention.

TECHNICAL FIELD

The disclosure relates to compounds and methods for treating neurodegenerative diseases.

BACKGROUND

Originally reported as anti-fungal agents, microtubule (MT)-active [1,2,4]triazolo[1,5-a]pyrimidines and related heterocyclic molecules have since attracted attention as potential candidates for a variety of applications including cancer chemotherapy and neurodegenerative disease treatment. Cevipabulin (Compound 1) is a potent anti-cancer compound. This compound, like vincristine, can interact with tubulin heterodimers and interfere with the rate of exchange of the guanosine triphosphate (GTP) and, thus, competes with vincristine but not taxol or colchicine, for binding to MTs. See, Zhang, "Synthesis and SAR of [1,2,4]triazolo[1,5-a]pyrimidines, a class of anticancer agents with a unique mechanism of tubulin inhibition," J. Med. Chem., 2007, 50:319-27.

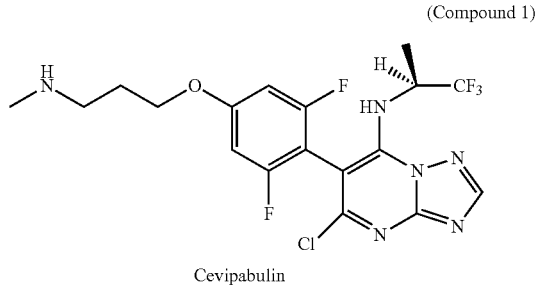 [SMILES: CNCCCOc1cc(F)c(-c2c(Cl)nc3ncnn3c2N[C@@H](C)C(F)(F)F)c(F)c1]

(Compound 1)
Cevipabulin

Opposite to the activity of vincristine/vinblastine, triazolopyrimidine Compound 2, binds exclusively to MTs and not to unpolymerized tubulin heterodimers. See, Sáez-Calvo, "Triazolopyrimidines Are Microtubule-Stabilizing Agents that Bind the *Vinca* Inhibitor Site of Tubulin," Cell Chemical Biology, 2017, 24, 737-750 e6.

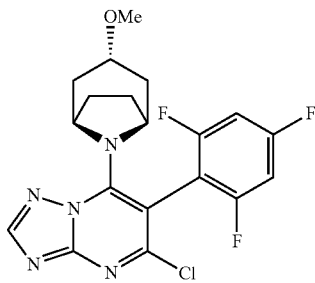

Compound 2

Triazolopyrimidine structural modifications can promote MT stabilization or disrupt MT integrity. These differences can have important and unknown ramifications in the therapeutic applications of triazolopyrimidines, including exhibiting different binding modes.

Thus, appropriately substituted triazolopyrimidines compounds for treating neurodegenerative disease are needed.

SUMMARY

In some embodiments, the present disclosure provides compounds of formula (I) or (II) or a pharmaceutically acceptable salt or stereoisomer thereof, wherein $R^1$-$R^8$ are defined herein. In other embodiments, the compound is of formula (I). In further embodiments, the compound is of formula (II).

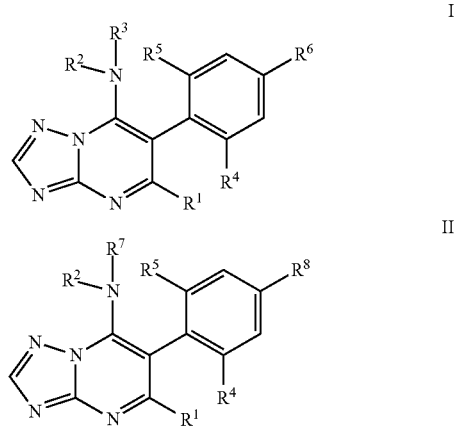

In other embodiments, the present disclosure provides compositions comprising a compound described herein and a pharmaceutically acceptable excipient.

In further embodiments, the present disclosure provides methods of stabilizing microtubules in a patient comprising administering to the patient a microtubule-stabilizing amount of a compound described herein.

In yet other embodiments, the present disclosure provides methods of treating cancer in a patient comprising administering to the patient a therapeutically effective amount of a compound described herein. In some aspects, the cancer is breast cancer, uterine cancer, lung cancer, ovarian cancer, and skin cancer, or non-Hodgkin's lymphoma.

In further embodiments, the present disclosure provides methods of treating a neurodegenerative disease in a patient comprising administering to the patient a therapeutically effective amount of a compound described herein. In some aspects, the neurodegenerative disease is characterized by a tauopathy or compromised microtubule function in the brain of the patient. In other aspects, the neurodegenerative disease is Alzheimer's disease, frontotemporal lobar degeneration, Pick's disease, progressive supranuclear palsy (PSP), corticobasal degeneration, Parkinson's disease (PD), PD with dementia, Lewy body disease with dementia, or amyotrophic lateral sclerosis. In further aspects, the neurodegenerative disease is traumatic brain injury, in particular, repetitive traumatic brain injury and chronic traumatic encephalopathy, or post-traumatic stress disorder. In yet other aspects, the neurodegenerative disease is schizophrenia.

Other aspects and embodiments of the invention will be readily apparent from the following detailed description of the invention.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific compositions, methods, devices, and systems disclosed. In addition, the drawings are not necessarily drawn to scale.

FIG. 1 is a bar graph showing the relative changes of acetylated α-tubulin (A) and total α-tubulin (B) caused by compound 22 in HEK-293 cells after 4 h of incubation. **, $p<0.01$ as determined by one-way ANOVA and Dunnett's post-hoc analysis.

DETAILED DESCRIPTION OF ILLUSTRATIVE EMBODIMENTS

In the present disclosure the singular forms "a", "an" and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant FIGURES used for a particular value may be one non-limiting method of determining the extent of the word "about". In other cases, the gradations used in a series of values may be used to determine the intended range available to the term "about" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

The term "alkyl," when used alone or as part of a substituent group, refers to a straight- or branched-chain alkyl group having from 1 to 12 carbon atoms ("$C_{1-12}$"), preferably 1 to 6 carbons atoms ("$C_{1-6}$"), in the chain. Examples of alkyl groups include methyl (Me, $C_1$alkyl) ethyl (Et, $C_2$alkyl), n-propyl ($C_3$alkyl), isopropyl ($C_3$alkyl), butyl ($C_4$alkyl), isobutyl ($C_4$alkyl), sec-butyl ($C_4$alkyl), tert-butyl ($C_4$alkyl), pentyl ($C_5$alkyl), isopentyl ($C_5$alkyl), tert-pentyl ($C_5$alkyl), hexyl ($C_6$alkyl), isohexyl ($C_6$alkyl), and groups that in light of the ordinary skill in the art and the teachings provided herein would be considered equivalent to any one of the foregoing examples. An alkyl moiety is optionally substituted with one, two, or three substituents selected from halo (F, Cl, Br, or I, preferably F), —OH, —$OC_{1-6}$alkyl, —CN, —$NH_2$, —NH($C_{1-6}$alkyl), —NH($C_{1-6}$alkyl)$_2$, $C_{3-8}$cycloalkyl, heterocyclyl, aryl, or heteroaryl.

The term "$C_{1-6}$alk" refers to an aliphatic linker having 1, 2, 3, 4, 5, or 6 carbon atoms and includes, for example, —$CH_2$—, —$CH(CH_3)$—, —$CH(CH_3)$—$CH_2$—, and —$C(CH_3)_2$—. The term "—$C_0$alk-" refers to a bond.

The term "haloalkyl," when used alone or as part of a substituent group, refers to an alkyl group as described above having one, two, or three halogen atoms attached to a single carbon atom. Preferably, the halogen is F. In some embodiments, haloalkyl includes perfluoroalkyl groups whereby the alkyl group is terminated with a $CF_3$, $CH_2F$, or $CHF_2$. Examples of alkyl groups include $CF_3$, $CHF_2$, $CH_2F$, $CHF_2$, $CH_2CF_3$, $CHFCF_3$, $CF_2CF_3$, $CH_2CHF_2$, $CH_2CH_2F$, $CHFCH_3$, $CF_2CH_3$, $CHFCHF_2$, $CF_2CHF_2$, among others, and groups that in light of the ordinary skill in the art and the teachings provided herein would be considered equivalent to any one of the foregoing examples. A haloalkyl moiety is optionally substituted with one, two, or three substituents selected from —OH, —$OC_{1-6}$alkyl, —CN, —$NH_2$, —NH($C_{1-6}$alkyl), —NH($C_{1-6}$alkyl)$_2$, $C_{3-8}$cycloalkyl, heterocyclyl, aryl, or heteroaryl.

The term "alkoxy," when used alone or as part of a substituent group, refers to a straight- or branched-chain alkoxy group, i.e., O-alkyl, having from 1 to 12 carbon atoms ("$C_{1-12}$"), preferably 1 to 6 carbons atoms ("$C_{1-6}$"), in the chain. Examples of alkoxy groups include methoxy (OMe, $C_1$alkoxy) ethoxy (OEt, $C_2$alkoxy), n-propoxy (O$^n$Pr, $C_3$alkoxy), isopropoxy (O$^i$Pr, $C_3$alkoxy), butoxy (OBu, $C_4$alkoxy), isobutoxy (O$^i$Bu, $C_4$alkoxy), sec-butoxy (O$^s$Bu, $C_4$alkoxy), tert-butoxy (O$^t$Bu, $C_4$alkoxy), pentoxy ($C_5$alkoxy), isopentoxy ($C_5$alkoxy), tert-pentoxy ($C_5$alkoxy), hexoxy ($C_6$alkoxy), isohexoxy ($C_6$alkoxy), and groups that in light of the ordinary skill in the art and the teachings provided herein would be considered equivalent to any one of the foregoing examples. An alkoxy moiety is optionally substituted with one, two, or three substituents selected from halo (F, Cl, Br, or I, preferably F), —OH, —CN, —NH$_2$, —NH(C$_{1-6}$alkyl), —NH(C$_{1-6}$alkyl)$_2$, C$_{3-8}$cycloalkyl, heterocyclyl, aryl, or heteroaryl.

"Heterocyclyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18: refers to each integer in the given range, e.g., "3 to 18 ring atoms" means that the heterocyclyl group may consist of 3 ring atoms, 4 ring atoms, etc., up to and including 18 ring atoms. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of heterocyclyl radicals include, but are not limited to, azepanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. "Heterocyclyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic. A heterocyclyl moiety is optionally substituted with one, two, or three substituents selected from halo (F, Cl, Br, or I, preferably F), —OH, —OC$_{1-6}$alkyl, —CN, —NH$_2$, —NH(C$_{1-6}$alkyl), —NH(C$_{1-6}$alkyl)$_2$, C$_{3-8}$cycloalkyl, heterocyclyl, aryl, or heteroaryl.

The term "cycloalkyl" refers to monocyclic, non-aromatic hydrocarbon groups having from 3 to 10 carbon atoms ("C$_{3-10}$"), preferably from 3 to 6 carbon atoms ("C$_3$-6"). Examples of cycloalkyl groups include, for example, cyclopropyl (C$_3$), cyclobutyl (C$_4$), cyclopentyl (C$_5$), cyclohexyl (C$_6$), 1-methylcyclopropyl (C$_4$), 2-methylcyclopentyl (C$_4$), adamantanyl (C$_{10}$), and the like. A cycloalkyl is optionally substituted with one, two, or three substituents selected from halo (F, Cl, Br, or I, preferably F), —OH, —OC$_{1-6}$alkyl, —CN, —NH$_2$, —NH(C$_{1-6}$alkyl), —NH(C$_{1-6}$alkyl)$_2$, C$_{3-8}$cycloalkyl, heterocyclyl, aryl, or heteroaryl.

The term "aryl" refers to carbocyclic aromatic groups having from 6 to 10 carbon atoms ('C$_{6-10}$") such as phenyl, naphthyl, and the like. An aryl is optionally substituted with one, two, or three substituents selected from halo (F, Cl, Br, or I, preferably F), —OH, —OC$_{1-6}$alkyl, —CN, —NH$_2$, —NH(C$_{1-6}$alkyl), —NH(C$_{1-6}$alkyl)$_2$, C$_{3-8}$cycloalkyl, heterocyclyl, aryl, or heteroaryl. In some embodiments, the aryl is substituted with one halo. In other embodiments, the aryl is substituted with one F. In further embodiments, the aryl is substituted with one $^{18}$F. In still other embodiments, the aryl is phenyl and is optionally substituted with one halo. In yet further embodiments, the aryl is phenyl and is optionally substituted with one F. In other embodiments, the aryl is phenyl and is optionally substituted with one $^{18}$F.

"Heteroaryl" refers to a 5- to 18-membered aromatic radical, e.g., C$_{5-18}$heteroaryl, that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range, e.g., "5 to 18 ring atoms" means that the heteroaryl group may contain 5 ring atoms, 6 ring atoms, etc., up to and including 18 ring atoms. An N-containing heteroaryl moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5] thieno[2,3-d]pyrimidinyl, 5,6-dihydrobenzo[h]quinazolinyl, 5,6-dihydrobenzo[h]cinnolinyl, 6,7-dihydro-5H-benzo[6,7] cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6, 6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d] pyrimidinyl, pyrido[3,4-d]pyrimidinyl, pyrazinyl, pyrimidinyl, pyridazinyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d] pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). A heteroaryl is optionally substituted with one, two, or three substituents selected from halo (F, Cl, Br, or I, preferably F), —OH, —OC$_{1-6}$alkyl, —CN, —NH$_2$, —NH(C$_{1-6}$alkyl), —NH(C$_{1-6}$alkyl)$_2$, C$_{3-8}$cycloalkyl, heterocyclyl, aryl, or heteroaryl.

When a range of carbon atoms is used herein, for example, C$_{1-6}$, all ranges, as well as individual numbers of carbon atoms are encompassed. For example, "C$_{1-3}$" includes C$_{1-3}$, C$_{1-2}$, C$_{2-3}$, C$_1$, C$_2$, and C$_3$.

The terms "halogen" and "halo" represent chlorine, fluorine, bromine, or iodine. The term "halo" represents chloro, fluoro, bromo, or iodo. When present in the compounds described herein, one or more halogen atom may be radiolabeled. In some embodiments, any $^{19}$F atom may be substituted with a $^{18}$F atom. In other embodiments, any $^{127}$I may be substituted with $^{123}$I. In further embodiments, any $^{127}$I may be substituted with $^{124}$I. In yet further embodiments, any $^{127}$I may be substituted with $^{125}$I. In still other embodiments, any $^{127}$I may be substituted with $^{131}$I. In other embodiments, any $^{80}$Br may be substituted with $^{76}$Br). In further embodiments, any $^{80}$Br may be substituted with $^{77}$Br.

"Compounds of the present disclosure," and equivalent expressions, are meant to embrace compounds of the Formulae (I) and (II) as described herein, which expression includes the pharmaceutically acceptable salts, where the context so permits. Similarly, reference to intermediates, whether or not they themselves are claimed, is meant to embrace their salts, and solvates, where the context so permits. Similarly, the term "compound(s) of formula (I)" includes those compounds of "formula (I)," as well as compounds of any of the formula (I) subgenera. The term "compound(s) of formula (II)" includes those compounds of "formula (II)," as well as compounds of any of the formula (II) subgenera.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

The terms "patient" or "subject" as used herein refer to a mammalian animal and are used interchangeably. In some embodiments, the patient or subject is a human. In other embodiments, the patient or subject is a veterinary or farm animal, a domestic animal or pet, or animal normally used for clinical research.

"Treating" any disease or disorder refers, in some embodiments, to ameliorating the disease or disorder (i.e., arresting or reducing the development of the disease or at least one of the clinical symptoms thereof). In some embodiments, "treating" or "treatment" refers to ameliorating at least one physical parameter, which may not be discernible by the subject. In other embodiments, "treating" or "treatment" refers to modulating the disease or disorder, either physically, (e.g., stabilization of a discernible symptom), physiologically, (e.g., stabilization of a physical parameter), or both. In further embodiments, "treating" or "treatment" refers to delaying the onset of the disease or disorder.

As used herein, the term "isotopic variant" refers to a compound that contains unnatural proportions of isotopes at one or more of the atoms that constitute such compound. For example, an "isotopic variant" of a compound can be radiolabeled, that is, contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the disclosure may include the preparation of isotopic variants with radioisotopes, in the instance for example, where the resulting compounds may be used for drug and/or substrate tissue distribution studies. Radiolabeled compounds of the disclosure can be used in diagnostic methods such as Single-photon emission computed tomography (SPECT). The radioactive isotopes tritium, i.e. $^3$H, and carbon-14, i.e. $^{14}$C, are particularly useful for their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers. The compounds of this disclosure may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. Within the present disclosure, any open valency appearing on a carbon, oxygen, or nitrogen atom in any structure described herein indicates the presence of a hydrogen atom. Where a chiral center exists in a structure, but no specific stereochemistry is shown for that center, both enantiomers, separately or as a mixture, are encompassed by that structure. The methods for the determination of stereochemistry and the separation of stereoisomers are well-known in the art.

The [1,2,4]triazolo[1,5-a]pyrimidine compounds described herein are a promising class of non-naturally occurring microtubule (MT)-active compounds. These molecules either promote stabilization of MTs or disrupt MT integrity. In some embodiments, the compounds are of formula (I) or (II) or a pharmaceutically acceptable salt or stereoisomer thereof. In further embodiments, the disclosure provides a pharmaceutically acceptable salt of a compound of formula (I) or (II). In other embodiments, the disclosure provides a stereoisomer of a compound of formula (I) or (II). In still other embodiments, the compounds are of formula (I). In yet further embodiments, the compounds are of formula (II).

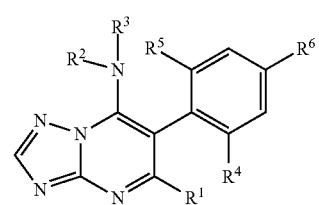

I

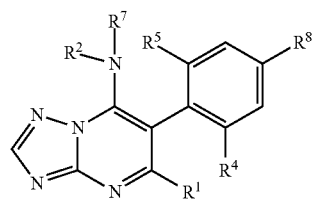

II

In these compounds, R$^1$ is H, Br, Cl, or F. In some embodiments, R$^1$ is H. In other embodiments, R$^1$ is Br, Cl, or F. In further embodiments, R$^1$ is Br. In yet other embodiments, R$^1$ is Cl. In still further embodiments, R$^1$ is F.

R$^2$ is H, C$_{1-6}$alkyl, or substituted C$_{1-6}$alkyl. In some embodiments, R$^2$ is H. In other embodiments, R$^2$ is C$_{1-6}$alkyl. In further embodiments, R$^2$ is methyl, ethyl, propyl, butyl, pentyl, or hexyl. In yet further embodiments, R$^2$ is methyl. In yet other embodiments, R$^2$ is ethyl. In still other embodiments, R$^2$ is propyl. In further embodiments, R$^2$ is butyl. In other embodiments, $R^2$ is pentyl. In still other embodiments, $R^2$ is hexyl. In further embodiments, $R^2$ is substituted $C_{1-6}$alkyl.

$R^4$ is H, Br, Cl, or F. In some embodiments, $R^4$ is H. In other embodiments, $R^4$ is Br, Cl, or F. In further embodiments, $R^4$ is Br. In still other embodiments, $R^4$ is Cl. In yet further embodiments, $R^4$ is F.

$R^5$ is H, Br, Cl, or F. In some embodiments, $R^5$ is H. In other embodiments, $R^5$ is Br, Cl, or F. In further embodiments, $R^5$ is Br. In still other embodiments, $R^5$ is Cl. In yet further embodiments, $R^5$ is F.

For the compounds of formula (I), $R^3$ is diazirinyl, $C_{1-6}$alkyl, halogenated $C_{1-6}$alkyl, $C_{1-6}$alkyl substituted with diazirinyl, aryl substituted with diazirinyl, or C(O)(aryl substituted with diazirinyl). In some embodiments, $R^3$ is $C_{1-6}$alkyl. In further embodiments, $R^3$ is methyl. In other embodiments, $R^3$ is ethyl. In further embodiments, $R^3$ is propyl. In yet other embodiments, $R^3$ is butyl. In still further embodiments, $R^3$ is pentyl. In yet other embodiments, $R^3$ is hexyl.

In further embodiments, $R^3$ is halogenated $C_{1-6}$alkyl. In other embodiments, $R^3$ is halogenated methyl, halogenated ethyl, halogenated propyl, halogenated butyl, halogenated pentyl, or halogenated hexyl. In yet further embodiments, $R^3$ is $CH_2CF_3$, $CH_2CH_2CF_3$, $CH(CH_3)(CF_3)$, $CH_2CH_2CH_2CF_3$, $CH_2CH(CF_3)CH_3$, or $CH(CF_3)CH_2CH_3$. In other embodiments, $R^3$ is $CH_2CF_3$. In further embodiments, $R^3$ is $CH_2CH_2CF_3$. In yet other embodiments, $R^3$ is $CH(CH_3)(CF_3)$. In still further embodiments, $R^3$ is $CH_2CH_2CH_2CF_3$. In other embodiments, $R^3$ is $CH_2CH(CF_3)CH_3$. In further embodiments, $R^3$ is $CH(CF_3)CH_2CH_3$.

In other embodiments, $R^3$ is diazirinyl. In still further embodiments, $R^3$ is diazirinyl such as

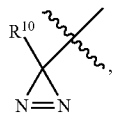

wherein $R^{10}$ is H, $C_{1-6}$alkyl, or halogenated $C_{1-6}$alkyl. In some embodiments, $R^{10}$ is H. In other embodiments, $R^{10}$ is $C_{1-6}$alkyl. In further embodiments, $R^{10}$ is methyl. In yet other embodiments, $R^{10}$ is ethyl. In still further embodiments, $R^{10}$ is propyl. In other embodiments, $R^{10}$ is butyl. In further embodiments, $R^{10}$ is pentyl. In yet other embodiments, $R^{10}$ is hexyl. In still other embodiments, $R^{10}$ is halogenated $C_{1-6}$alkyl. In further embodiments, $R^{10}$ is halogenated methyl, halogenated ethyl, halogenated propyl, halogenated butyl, halogenated pentyl, or halogenated hexyl. In yet further embodiments, $R^{10}$ is $CF_3$.

In other embodiments, $R^3$ is $C_{1-6}$ alkyl substituted with diazirinyl such as

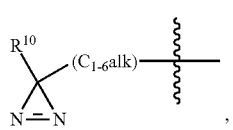

wherein $R^{10}$ is H, $C_{1-6}$alkyl, or halogenated $C_{1-6}$alkyl. In other embodiments, $R^3$ is

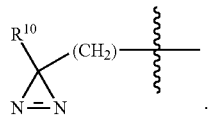

In further embodiments, $R^3$ is

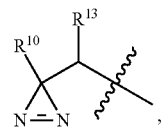

wherein $R^{13}$ is $C_{1-5}$alkyl such as methyl, ethyl, propyl, butyl, or pentyl, preferably methyl. In still other embodiments, $R^3$ is

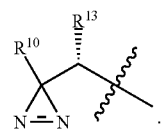

In yet further embodiments, $R^3$ is

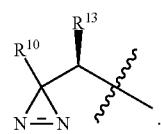

In other embodiments, $R^3$ is

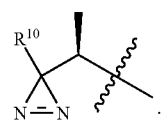

In yet other embodiments, $R^3$ is

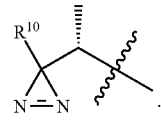

In still further embodiments, $R^3$ is

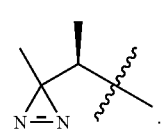

In other embodiments, $R^3$ is

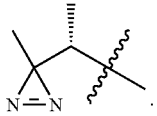

In further embodiments, $R^{10}$ is H. In other embodiments, $R^{10}$ is $C_{1-6}$alkyl. In further embodiments, $R^{10}$ is methyl. In yet other embodiments, $R^{10}$ is ethyl. In still further embodiments, $R^{10}$ is propyl. In other embodiments, $R^{10}$ is butyl. In further embodiments, $R^{10}$ is pentyl. In yet other embodiments, $R^{10}$ is hexyl. In still other embodiments, $R^{10}$ is halogenated $C_{1-6}$alkyl. In further embodiments, $R^{10}$ is halogenated methyl, halogenated ethyl, halogenated propyl, halogenated butyl, halogenated pentyl, or halogenated hexyl. In yet further embodiments, $R^{10}$ is $CF_3$.

In further embodiments, $R^3$ is aryl substituted with diazirinyl. In other embodiments, $R^3$ is phenyl substituted with diazirinyl. In still further embodiments, $R^3$ is

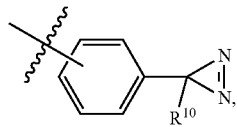

wherein $R^{10}$ is H, $C_{1-6}$alkyl, or halogenated $C_{1-6}$alkyl. In some embodiments, $R^{10}$ is H. In other embodiments, $R^{10}$ is $C_{1-6}$alkyl. In further embodiments, $R^{10}$ is methyl. In yet other embodiments, $R^{10}$ is ethyl. In still further embodiments, $R^{10}$ is propyl. In other embodiments, $R^{10}$ is butyl. In further embodiments, $R^{10}$ is pentyl. In yet other embodiments, $R^{10}$ is hexyl. In still other embodiments, $R^{10}$ is halogenated $C_{1-6}$alkyl. In further embodiments, $R^{10}$ is halogenated methyl, halogenated ethyl, halogenated propyl, halogenated butyl, halogenated pentyl, or halogenated hexyl. In yet further embodiments, $R^{10}$ is $CF_3$.

In still other embodiments, $R^3$ is C(O)(aryl substituted with diazirinyl). In further embodiments, $R^3$ is C(O)(phenyl substituted with diazirinyl). In other embodiments, $R^3$ is

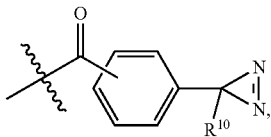

wherein $R^{10}$ is H, $C_{1-6}$alkyl, or halogenated $C_{1-6}$alkyl. In some embodiments, $R^{10}$ is H. In other embodiments, $R^{10}$ is $C_{1-6}$alkyl. In further embodiments, $R^{10}$ is methyl. In yet other embodiments, $R^{10}$ is ethyl. In still further embodiments, $R^{10}$ is propyl. In other embodiments, $R^{10}$ is butyl. In further embodiments, $R^{10}$ is pentyl. In yet other embodiments, $R^{10}$ is hexyl. In still other embodiments, $R^{10}$ is halogenated $C_{1-6}$alkyl. In further embodiments, $R^{10}$ is halogenated methyl, halogenated ethyl, halogenated propyl, halogenated butyl, halogenated pentyl, or halogenated hexyl. In yet further embodiments, $R^{10}$ is $CF_3$.

In the compounds of Formula (I), $R^6$ is halogen, $C_{1-6}$alkoxy, or substituted $C_{1-6}$alkoxy. In some embodiments, $R^6$ is halogen. In other embodiments $R^6$ is Br, Cl, or F. In further embodiments, $R^6$ is Br. In yet other embodiments, $R^6$ is Cl. In still further embodiments, $R^6$ is F. In other embodiments, $R^6$ is $C_{1-6}$alkoxy. In yet other embodiments, $R^6$ is methoxy. In still further embodiments, $R^6$ is ethoxy. In other embodiments, $R^6$ is propoxy. In further embodiments, $R^6$ is butoxy. In yet other embodiments, $R^6$ is pentoxy. In still further embodiments, $R^6$ is hexoxy. In yet other embodiments, $R^6$ is substituted alkoxy. In further embodiments, $R^6$ is substituted methoxy. In other embodiments, $R^6$ is substituted ethoxy. In still further embodiments, $R^6$ is substituted propoxy. In yet other embodiments, $R^6$ is substituted butoxy. In further embodiments, $R^6$ is substituted pentoxy. In other embodiments, $R^6$ is substituted hexoxy. In further embodiments, $R^6$ is $C_{1-6}$alkoxy substituted with diazirinyl. In further embodiments, $R^6$ is $C_{1-6}$alkoxy substituted with

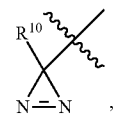

wherein $R^{10}$ is H, $C_{1-6}$alkyl, or halogenated $C_{1-6}$alkyl. In some embodiments, $R^{10}$ is H. In other embodiments, $R^{10}$ is $C_{1-6}$alkyl. In further embodiments, $R^{10}$ is methyl. In yet other embodiments, $R^{10}$ is ethyl. In still further embodiments, $R^{10}$ is propyl. In other embodiments, $R^{10}$ is butyl. In further embodiments, $R^{10}$ is pentyl. In yet other embodiments, $R^{10}$ is hexyl. In still other embodiments, $R^{10}$ is halogenated $C_{1-6}$alkyl. In further embodiments, $R^{10}$ is halogenated methyl, halogenated ethyl, halogenated propyl, halogenated butyl, halogenated pentyl, or halogenated hexyl. In yet further embodiments, $R^{10}$ is $CF_3$.

In the compounds of formula (II), $R^7$ is H, $C_{1-6}$alkyl, or halogenated $C_{1-6}$alkyl. In some embodiments, $R^7$ is H. In other embodiments, $R^7$ is $C_{1-6}$alkyl. In yet further embodiments, $R^7$ is methyl. In yet other embodiments, $R^7$ is ethyl. In still other embodiments, $R^7$ is propyl. In further embodiments, $R^7$ is butyl. In other embodiments, $R^7$ is pentyl. In still other embodiments, $R^7$ is hexyl. In further embodiments, $R^7$ is halogenated $C_{1-6}$alkyl. In yet further embodiments, $R^7$ is halogenated methyl, halogenated ethyl, halogenated propyl, halogenated butyl, halogenated pentyl, or halogenated hexyl. In other embodiments, $R^7$ is $CH_2CF_3$, $CH_2CH_2CF_3$, $CH(CH_3)CF_3$, $CH_2CH_2CH_2CF_3$, $CH_2CH(CF_3)CH_3$, or $CH(CF_3)CH_2CH_3$. In yet further embodiments, $R^7$ is $CH_2CF_3$, $CH_2CH_2CF_3$, $CH(CH_3)(CF_3)$, $CH_2CH_2CH_2CF_3$, $CH_2CH(CF_3)CH_3$, or $CH(CF_3)CH_2CH_3$. In other embodiments, $R^7$ is $CH_2CF_3$. In further embodiments, $R^7$ is $CH_2CH_2CF_3$. In yet other embodiments, $R^7$ is $CH(CH_3)CF_3$. In still further embodiments, $R^7$ is $CH_2CH_2CH_2CF_3$. In other embodiments, $R^7$ is $CH_2CH(CF_3)CH_3$. In further embodiments, $R^7$ is $CH(CF_3)CH_2CH_3$.

In the compounds of formula (II), $R^8$ is —O—$C_{1-6}$alk-$NR^9$—C(O)-aryl substituted by diazirinyl or —O-substituted $C_{1-6}$alk-$NR^9$—C(O)-aryl substituted by diazirinyl, wherein $R^9$ is H or $C_{1-6}$alkyl. In some embodiments, R9 is H. In other embodiments, $R^9$ is $C_{1-6}$alkyl. In yet further embodiments, $R^9$ is methyl. In yet other embodiments, $R^9$ is ethyl. In still other embodiments, $R^9$ is propyl. In further embodiments, $R^9$ is butyl. In other embodiments, $R^9$ is pentyl. In still other embodiments, $R^7$ is hexyl.

In some embodiments, $R^8$ is —O—$C_{1-6}$alk-$NR^9$—C(O)-aryl substituted by diazirinyl. In other embodiments, $R^8$ is —O—$C_{1-6}$alk-$NR^9$—C(O)-aryl substituted by

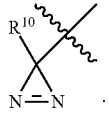

In further embodiments, $R^8$ is —O—$C_{1-6}$alk-$NR^9$—C(O)-phenyl substituted by

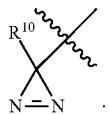

In further embodiments, $R^8$ is —O-substituted $C_{1-6}$alk-C(O)-aryl substituted by diazirinyl. In other embodiments, $R^8$ is —O-substituted $C_{1-6}$alk-C(O)-phenyl substituted by diazirinyl. In still further embodiments, $R^8$ is —O-substituted $C_{1-6}$alk-C(O)-aryl substituted by

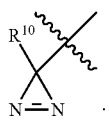

For each diazirinyl ring comprising an $R^{10}$ group, $R^{10}$ is H, $C_{1-6}$alkyl, or halogenated $C_{1-6}$alkyl. In some embodiments, $R^{10}$ is H. In other embodiments, $R^{10}$ is $C_{1-6}$ alkyl. In further embodiments, $R^{10}$ is methyl. In still other embodiments, $R^{10}$ is halogenated $C_{1-6}$alkyl. In yet further embodiments, $R^{10}$ is $CF_3$.

In some aspects, the compounds described herein are of formula (IA), wherein $R^1$, $R^2$, $R^5$, $R^6$, and $R^{10}$ are defined herein.

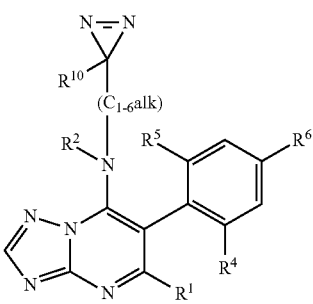

IA

In other aspects, the compounds described herein are of formula (IB), wherein $R^1$, $R^2$, $R^4$, and $R^{10}$ are defined herein:

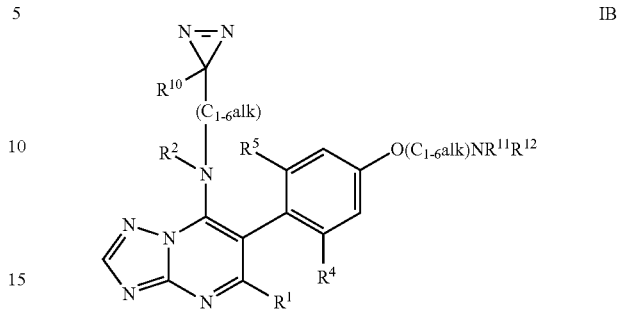

IB

In this structure, $R^{11}$ is H, $C_{1-6}$alkyl, or halogenated $C_{1-6}$alkyl. In some embodiments, $R^{11}$ is H. In other embodiments, $R^{11}$ is $C_{1-6}$alkyl. In further embodiments, $R^{11}$ is methyl. In still other embodiments, $R^{11}$ is halogenated $C_{1-6}$alkyl. In yet further embodiments, $R^{11}$ is $CF_3$. $R^{12}$ is H, $C_{1-6}$alkyl, or halogenated $C_{1-6}$alkyl. In some embodiments, $R^{12}$ is H. In other embodiments, $R^{12}$ is $C_{1-6}$alkyl. In further embodiments, $R^{12}$ is methyl. In yet other embodiments, $R^{12}$ is ethyl. In still other embodiments, $R^{12}$ is propyl. In further embodiments, $R^{12}$ is butyl. In other embodiments, $R^{12}$ is pentyl. In still other embodiments, $R^{12}$ is hexyl. In still other embodiments, $R^{12}$ is halogenated $C_{1-6}$alkyl. In yet further embodiments, $R^{12}$ is halogenated methyl. In yet other embodiments, $R^2$ is halogenated ethyl. In still other embodiments, $R^{12}$ is halogenated propyl. In further embodiments, $R^{12}$ is halogenated butyl. In other embodiments, $R^{12}$ is halogenated pentyl. In still other embodiments, $R^{12}$ is halogenated hexyl. In yet further embodiments, $R^{12}$ is $CF_3$.

In further aspects, the compound is of formula (IIA), wherein $R^1$-$R^5$ and $R^{10}$ are defined herein:

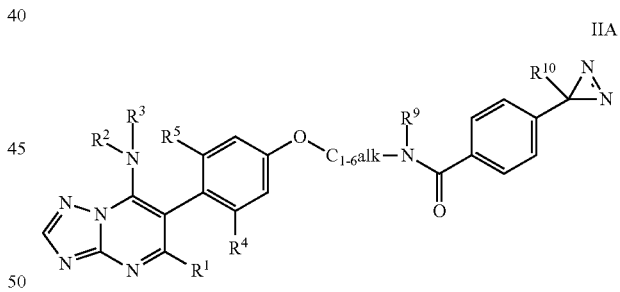

IIA

In this structure, $R^9$ is H, $C_{1-6}$alkyl, or substituted $C_{1-6}$alkyl. In some embodiments, $R^9$ is H. In other embodiments, $R^9$ is $C_{1-6}$alkyl. In further embodiments, $R^9$ is methyl. In yet other embodiments, $R^9$ is ethyl. In still other embodiments, $R^9$ is propyl. In further embodiments, $R^9$ is butyl. In other embodiments, $R^9$ is pentyl. In still other embodiments, $R^9$ is hexyl. In further embodiments, $R^9$ is substituted $C_{1-6}$alkyl. In yet further embodiments, $R^9$ is substituted methyl. In yet other embodiments, $R^9$ is substituted ethyl. In still other embodiments, $R^9$ is substituted propyl. In further embodiments, $R^9$ is substituted butyl. In other embodiments, $R^9$ is substituted pentyl. In still other embodiments, $R^9$ is substituted hexyl.

The disclosure also provides pharmaceutical compositions that contain a compound discussed herein in a pharmaceutically acceptable excipient. In some embodiments, a compound described above is present in a single composition. In other embodiments, a compound described above is combined with one or more excipients and/or other therapeutic agents as described below.

The compounds discussed above may encompass tautomeric forms of the structures provided herein characterized by the bioactivity of the drawn structures. Further, the compounds may also be used in the form of salts derived from pharmaceutically or physiologically acceptable acids, bases, alkali metals and alkaline earth metals.

In some embodiments, pharmaceutically acceptable salts can be formed from organic and inorganic acids including, e.g., acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids.

In other embodiments, pharmaceutically acceptable salts may also be formed from inorganic bases, desirably alkali metal salts including, e.g., sodium, lithium, or potassium, such as alkali metal hydroxides. Examples of inorganic bases include, without limitation, sodium hydroxide, potassium hydroxide, calcium hydroxide, and magnesium hydroxide. Pharmaceutically acceptable salts may also be formed from organic bases, such as ammonium salts, mono-, di-, and trimethylammonium, mono-, di- and triethylammonium, mono-, di- and tripropylammonium, ethyldimethylammonium, benzyldimethylammonium, cyclohexylammonium, benzyl-ammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1 n-butyl piperidinium, 2-methylpiperidinium, 1-ethyl-2-methylpiperidinium, mono-, di- and triethanolammonium, ethyl diethanolammonium, n-butylmonoethanolammonium, tris (hydroxymethyl)methylammonium, phenylmono-ethanolammonium, diethanolamine, ethylenediamine, and the like. In one example, the base is selected from among sodium hydroxide, lithium hydroxide, potassium hydroxide, and mixtures thereof.

The disclosure also provides pharmaceutical compositions that contain a compound discussed herein in a pharmaceutically acceptable excipient. The term "pharmaceutically acceptable excipient" as used herein refers to an excipient that is stable and compatible with a patient. In some embodiments, a compound described above is combined with one or more pharmaceutically acceptable excipients and/or other therapeutic agents as described below.

The pharmaceutical compositions include a compound described herein formulated neat or with one or more pharmaceutically acceptable excipients for administration, the proportion of which is determined by the solubility and chemical nature of the compound, chosen route of administration and standard pharmacological practice. The pharmaceutically acceptable excipient may be solid or liquid.

The compound may be administered to a subject by any desirable route, taking into consideration the specific condition for which it has been selected. The compound may, therefore, be delivered orally, by injection, i.e., transdermally, intravenously, subcutaneously, intramuscularly, intravenous, intra-arterial, intraperitoneal, intracavitary, or epiduraly, among others.

Although the compound may be administered alone, it may also be administered in the presence of one or more pharmaceutically acceptable excipient that are physiologically compatible. In some embodiments, the pharmaceutically acceptable excipient is a carrier.

The carrier may be in dry or liquid form and must be pharmaceutically acceptable. Liquid pharmaceutical compositions are typically sterile solutions or suspensions. When liquid carriers are utilized, they are desirably sterile liquids. Liquid carriers are typically utilized in preparing solutions, suspensions, emulsions, syrups and elixirs. In some embodiments, the compound is dissolved a liquid carrier. In some embodiments, the compound is suspended in a liquid carrier. One of skill in the art of formulations would be able to select a suitable liquid carrier, depending on the route of administration. In other embodiments, the liquid carrier includes, without limitation, water, organic solvents, oils, fats, or mixtures thereof. In yet other embodiments, the liquid carrier is water containing cellulose derivatives such as sodium carboxymethyl cellulose. In further embodiments, the liquid carrier is water and/or dimethylsulfoxide. Examples of organic solvents include, without limitation, alcohols such as monohydric alcohols and polyhydric alcohols, e.g., glycols and their derivatives, among others. Examples of oils include, without limitation, fractionated coconut oil, *arachis* oil, corn oil, peanut oil, and sesame oil and oily esters such as ethyl oleate and isopropyl myristate.

Alternatively, the compound may be formulated in a solid carrier. In some embodiments, the composition may be compacted into a unit dose form, i.e., tablet or caplet. In other embodiments, the composition may be added to unit dose form, i.e., a capsule. In further embodiments, the composition may be formulated for administration as a powder. The solid carrier may perform a variety of functions, i.e., may perform the functions of two or more of the pharmaceutically acceptable excipients described below. For example, the solid carrier may also act as a flavoring agent, lubricant, solubilizer, suspending agent, filler, glidant, compression aid, binder, disintegrant, or encapsulating material. Suitable solid carriers include, without limitation, calcium phosphate, dicalcium phosphate, magnesium stearate, talc, starch, sugars (including, e.g., lactose and sucrose), cellulose (including, e.g., microcrystalline cellulose, methyl cellulose, sodium carboxymethyl cellulose), polyvinylpyrrolidine, low melting waxes, ion exchange resins, and kaolin. The solid carrier can contain other suitable pharmaceutically acceptable excipients, including those described below.

Examples of pharmaceutically acceptable excipients which may be combined with the compound include, without limitation, adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, suspending agents, syrups, thickening agents, or viscosity regulators. See, the excipients described in the "Handbook of Pharmaceutical Excipients", 5th Edition, Eds.: Rowe, Sheskey, and Owen, APhA Publications (Washington, D.C.), Dec. 14, 2005, which is incorporated herein by reference.

The pharmaceutical composition described herein may be prepared by those skilled in the art. In some embodiments, the pharmaceutical compositions are prepared by combining a compound described herein with a pharmaceutically acceptable excipient.

The compounds described herein are useful in stabilizing microtubules. As such, these compounds are useful in treating diseases that are modulated by microtubules. In some embodiments, the compounds described herein are useful in treating neurodegenerative diseases. Thus, the compounds may be useful in treating neurodegenerative diseases which are characterized by a tauopathy or compromised microtubule function in a subject, such as in the brain of the subject. In some embodiments, the compounds are useful for treating Alzheimer's disease, frontotemporal lobar degeneration, Pick's disease, progressive supranuclear palsy (PSP), corticobasal degeneration, schizophrenia, Parkinson's disease (PD), PD with dementia, Lewy body disease with dementia, amyotrophic lateral sclerosis, argyrophilic grain disease, chronic traumatic encephalopathy, diffuse neurofibrillary tangles with calcification, Down's syndrome, Familial British dementia, Familial Danish dementia, frontotemporal dementia, parkinsonism linked to chromosome 17, Gerstmann-Straussler-Scheinker disease, Guadeloupean parkinsonism, multiple sclerosis, myotonic dystrophy, neurodegeneration with brain iron accumulation, Niemann-Pick disease, type C, non-Guamanian motor neuron disease with neurofibrillary tangles, postencephalitic parkinsonism, prion protein cerebral amyloid angiopathy, progressive subcortical gliosis, SLC9A6-related mental retardation, subacute sclerosing panencephalitis, tangle-only dementia, white matter tauopathy with globular glial inclusions. In other embodiments, the compounds can be used to treat traumatic brain injury (TBI), especially repetitive TBI (rTBI), such as that due to dementia pugilistica and recurrent football concussions and military closed head injuries such as that due to IEDs, which also is known as chronic traumatic encephalopathy (CTE), with features of tauopathy or AD-like pathology or post-traumatic stress disorder. In some embodiments, the compounds are useful in treating Alzheimer's disease. In other embodiments, the compounds are useful in treating schizophrenia.

In other embodiments, the compounds are useful for treating cancer. The term "cancer" as used herein, refers to neoplastic cells in a patient which have abnormal cell group and invade or have the potential to invade one or more body parts of the patient. In some embodiments, the cancer is breast cancer, uterine cancer, lung cancer, ovarian cancer, and skin cancer, or non-Hodgkin's lymphoma. In other embodiments, the cancer is breast cancer. In further embodiments, the cancer is uterine cancer. In other embodiments, the cancer is lung cancer. In yet other embodiments, the cancer is ovarian cancer. In still further embodiments, the cancer is skin cancer. In other embodiments, the cancer is non-Hodgkin's lymphoma.

In some embodiments, a therapeutically effective amount of a pharmaceutical agent according to the disclosure is administered to a subject suffering from or diagnosed as having such a disease, disorder, or condition. A "therapeutically effective amount" means an amount or dose sufficient to generally bring about the desired therapeutic benefit in patients in need of such treatment for the designated disease, disorder, or condition. The "therapeutically effective amount" may also mean the amount of the compound to stabilize microtubules. Therapeutically effective amounts or doses of the compounds of the present disclosure may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

These therapeutically effective amounts may be provided on regular schedule, i.e., daily, weekly, monthly, or yearly basis or on an irregular schedule with varying administration days, weeks, months, etc. Alternatively, the therapeutically effective amount to be administered may vary. In some embodiments, the therapeutically effective amount for the first dose is higher than the therapeutically effective amount for one or more of the subsequent doses. In other embodiments, the therapeutically effective amount for the first dose is lower than the therapeutically effective amount for one or more of the subsequent doses.

Also provided herein are kits or packages containing a compound or composition described herein. The kits may be organized to indicate a single formulation or combination of formulations to be taken at each desired time. The composition may also be sub-divided to contain appropriate quantities of the compound. For example, the unit dosage can be packaged compositions, e.g., packeted powders, vials, ampoules, prefilled syringes or sachets containing liquids.

Suitably, the kit contains packaging or a container with the compound formulated for the desired delivery route. Suitably, the kit contains instructions on dosing and an insert regarding the compound. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of the delivery device. Other suitable components to include in such kits will be readily apparent to one of skill in the art, taking into consideration the desired indication and the delivery route. The doses are repeated daily, weekly, or monthly, for a predetermined length of time or as prescribed.

The compound or composition described herein can be a single dose or for continuous or periodic discontinuous administration. For continuous administration, a package or kit can include the compound in each dosage unit (e.g., solution, lotion, tablet, pill, or other unit described above or utilized in drug delivery). When the compound is to be delivered with periodic discontinuation, a package or kit can include placebos during periods when the compound is not delivered. When varying concentrations of a composition, of the components of the composition, or of relative ratios of the compound or other agents within a composition over time is desired, a package or kit may contain a sequence of dosage units, so varying.

A number of packages or kits are known in the art for the use in dispensing pharmaceutical agents for oral use. In some embodiments, the package has indicators for each period. In other embodiments, the package is a labeled blister package, dial dispenser package, or bottle.

The packaging means of a kit may itself be geared for administration, such as an inhalant, syringe, pipette, eye dropper, or other such like apparatus, from which the formulation may be applied to an infected area of the body, such as the lungs, injected into a subject, or even applied to and mixed with the other components of the kit.

The compound or composition of these kits also may be provided in dried or lyophilized forms. When reagents or components are provided as a dried form, reconstitution generally is by the addition of a suitable solvent. It is envisioned that the solvent also may be provided in another packaging means.

The kits may include a means for containing the vials in close confinement for commercial sale such as, e.g., injection or blow-molded plastic containers into which the desired vials are retained.

Irrespective of the number or type of packages, the kits also may include, or be packaged with a separate instrument for assisting with the injection/administration or placement of the ultimate complex composition within the body of an animal. Such an instrument may be an inhalant, syringe, pipette, forceps, measuring spoon, eye dropper or any such medically approved delivery means. Other instrumentation includes devices that permit the reading or monitoring of reactions in vitro.

SAR of [1,2,4]triazolo[1,5-a]pyrimidines, a class of anticancer agents with a unique mechanism of tubulin inhibition," J. Med. Chem., 2007, 50, 319-27. (Scheme 1). Thus, azidated derivatives 6-8, in which the photoactivatable group is at C-5 (7 and 8) or C-7 (6), were accessed respectively from triazolopyrimidine 9, 10 and 1 upon reaction with sodium azide. Triazolopyrimidine derivative 11, which comprises an aryl diazirine fragment appended at the terminal amine of the alkoxy side chain, was readily accessed via N-acylation of compound 12 (Zhang cited above) with commercially available diazirine 13. Finally, triazolopyrimidine 14-16, which incorporate a diazirine ring into the amine fragment linked at C-5, were accessed from dichloride 9 upon reaction with the appropriate diazirine containing amine (17-19) that were prepared from N-Boc protected amino acids. Further reaction of 14-16 with the appropriate alkoxy side chain resulted in derivatives 20-22.

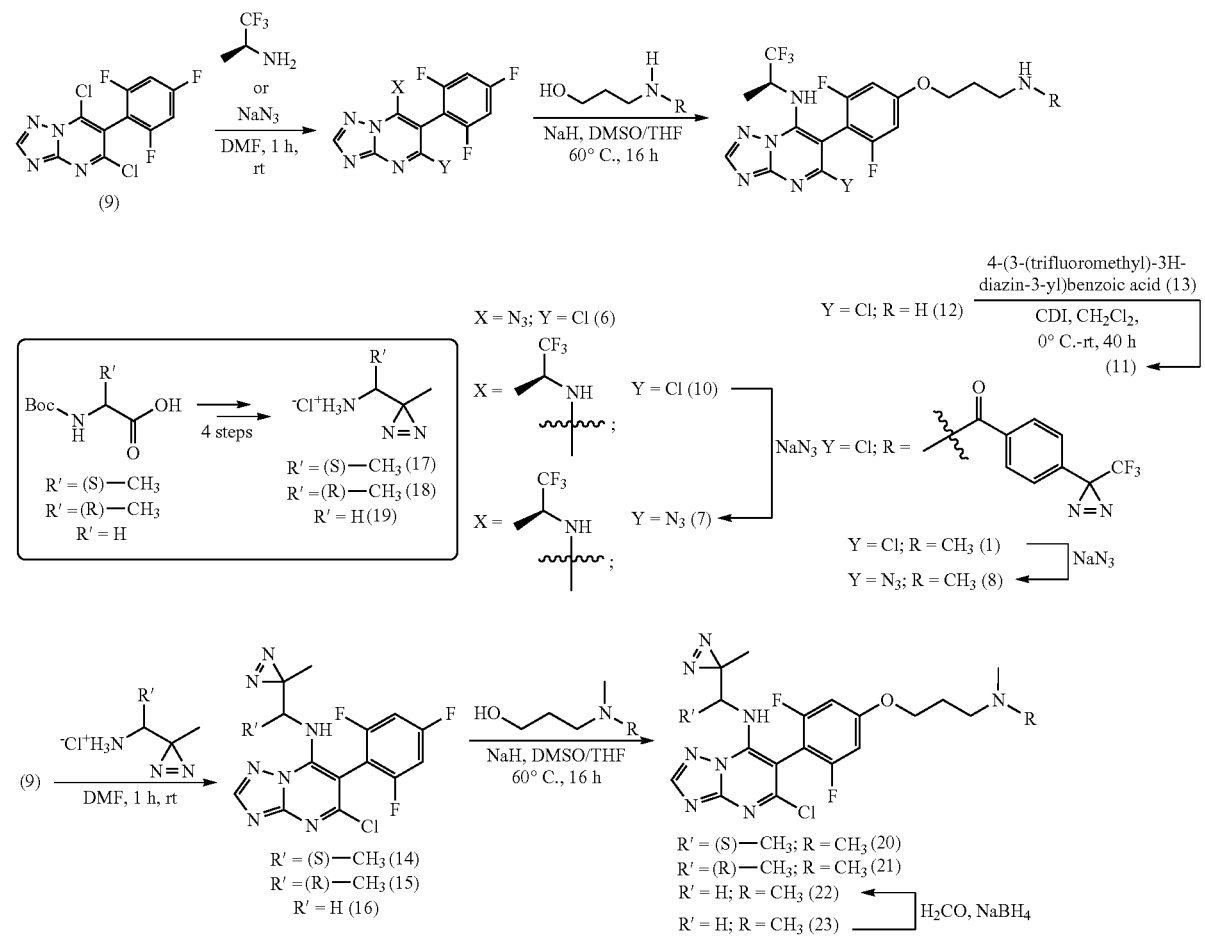

Scheme 1

In some embodiments, pharmaceutical kits are provided and contain a compound of formula (I) or (II). The compound may be in the presence or absence of one or more of the carriers or pharmaceutically effective excipients described above. The kit may optionally contain instructions for administering the compound to a subject having cancer.

The compounds may be prepared as described herein and using the procedures described in Zhang, "Synthesis and The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Aspects

Aspect 1: A compound of formula (I) or formula (II):

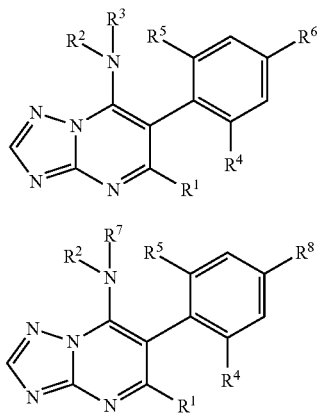

wherein:
- $R^1$ is H, Br, Cl, or F;
- $R^2$ is H, $C_{1-6}$alkyl, or substituted $C_{1-6}$alkyl;
- $R^3$ is diazirinyl, $C_{1-6}$alkyl, halogenated $C_{1-6}$alkyl, $C_{1-6}$alkyl substituted with diazirinyl, aryl substituted with diazirinyl, or C(O)(aryl substituted with diazirinyl);
- $R^4$ is H, Br, Cl, or F;
- $R^5$ is H, Br, Cl, or F;
- $R^6$ is halogen, $C_{1-6}$alkoxy, or substituted $C_{1-6}$alkoxy;
- $R^7$ is H, $C_{1-6}$alkyl, or halogenated $C_{1-6}$alkyl; and
- $R^8$ is —O—$C_{1-6}$alk-$NR^9$—C(O)-aryl substituted by diazirinyl or —O-substituted $C_{1-6}$alk-$NR^9$—C(O)-aryl substituted by diazirinyl, wherein $R^9$ is H or $C_{1-6}$alkyl;

or a pharmaceutically acceptable salt or stereoisomer thereof.

Aspect 2: The compound of aspect 1, that is of formula (I):

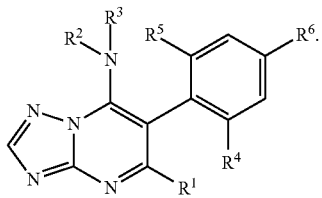

Aspect 3: The compound of aspect 1 or 2, wherein $R^1$ is H.

Aspect 4: The compound of aspect 1 or 2, wherein $R^1$ is Br, Cl, or F, preferably Cl.

Aspect 5: The compound of any one of aspects 2 to 4, wherein $R^2$ is H.

Aspect 6: The compound of any one of aspects 2 to 4, wherein $R^2$ is $C_{1-6}$alkyl such as methyl, ethyl, propyl, butyl, pentyl, or hexyl.

Aspect 7: The compound of any one of aspects 2 to 4, wherein $R^2$ is substituted $C_{1-6}$alkyl.

Aspect 8: The compound of any one of the preceding aspects, wherein $R^3$ is $C_{1-6}$alkyl such as methyl, ethyl, propyl, butyl, pentyl, or hexyl.

Aspect 9: The compound of any one of aspects 2 to 7, wherein $R^3$ is halogenated $C_{1-6}$alkyl such as $CH_2CF_3$, $CH_2CH_2CF_3$, $CH(CH_3)(CF_3)$, $CH_2CH_2CH_2CF_3$, $CH_2CH(CF_3)CH_3$, or $CH(CF_3)CH_2CH_3$, preferably $CH(CH_3)CF_3$.

Aspect 10: The compound of any one of aspects 2 to 7, wherein $R^3$ is diazirinyl such as

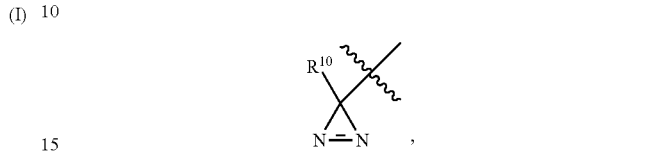

wherein $R^{10}$ is H, $C_{1-6}$alkyl, or halogenated $C_{1-6}$alkyl.

Aspect 11: The compound of any one of aspects 2 to 7, wherein $R^3$ is $C_{1-6}$alkyl substituted with diazirinyl such as

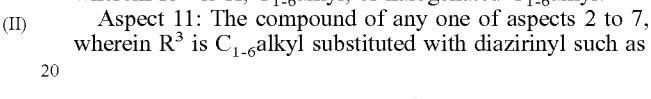

wherein $R^{10}$ is H, $C_{1-6}$alkyl, or halogenated $C_{1-6}$alkyl.

Aspect 12: The compound of any one of aspects 2 to 7, wherein $R^3$ is aryl substituted with diazirinyl such as phenyl substituted with diazirinyl, such as

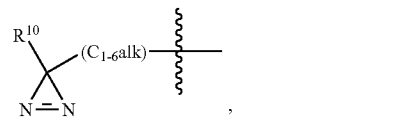

wherein $R^{10}$ is H, $C_{1-6}$alkyl, or halogenated $C_{1-6}$alkyl.

Aspect 13: The compound of any one of aspects 2 to 7, wherein $R^3$ is C(O)(aryl substituted with diazirinyl) such as phenyl substituted with diazirinyl, such as

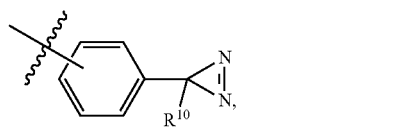

wherein $R^{10}$ is H, $C_{1-6}$alkyl, or halogenated $C_{1-6}$alkyl.

Aspect 14: The compound of any one of aspects 2 to 13, wherein $R^6$ is halogen such as Br, Cl, or F, preferably F.

Aspect 15: The compound of any one of aspects 2 to 13, wherein $R^6$ is $C_{1-6}$alkoxy such as methoxy, ethoxy, propoxy, butoxy, pentoxy, or hexoxy.

Aspect 16: The compound of any one of aspects 2 to 13, wherein $R^6$ is $C_{1-6}$alkoxy substituted with diazirinyl such as

wherein $R^{10}$ is H, $C_{1-6}$alkyl, or halogenated $C_{1-6}$alkyl.

Aspect 17: The compound of aspect 1, that is of formula (II):

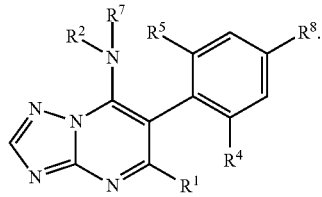

Aspect 18: The compound of aspect 21, wherein $R^1$ is H.

Aspect 19: The compound of aspect 21, wherein $R^1$ is Br, Cl, or F, preferably Cl.

Aspect 20: The compound of any one of aspects 17 to 19, wherein $R^2$ is H.

Aspect 21: The compound of any one of aspects 17 to 19, wherein $R^2$ is $C_{1-6}$alkyl such as methyl, ethyl, propyl, butyl, pentyl, or hexyl.

Aspect 22: The compound of any one of aspects 17 to 19, wherein $R^2$ is substituted $C_{1-6}$alkyl.

Aspect 23: The compound of any one of aspects 17 to 22, wherein $R^7$ is H.

Aspect 24: The compound of any one of aspects 17 to 22, wherein $R^7$ is $C_{1-6}$alkyl such as methyl, ethyl, propyl, butyl, pentyl, or hexyl.

Aspect 25: The compound of any one of aspects 17 to 22, wherein $R^7$ is halogenated $C_{1-6}$alkyl such as $CH_2CF_3$, $CH_2CH_2CF_3$, $CH(CH_3)(CF_3)$, $CH_2CH_2CH_2CF_3$, $CH_2CH(CF_3)CH_3$, or $CH(CF_3)CH_2CH_3$, preferably $CH(CH_3)CF_3$.

Aspect 26: The compound of any one of aspects 17 to 25, wherein $R^8$ is —O—$C_{1-6}$alk-$NR^9$—C(O)-aryl substituted by diazirinyl such as

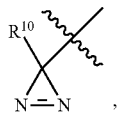

wherein $R^{10}$ is H, $C_{1-6}$alkyl, or halogenated $C_{1-6}$alkyl.

Aspect 27: The compound of any one of aspects 17 to 25, wherein $R^8$ is —O-substituted $C_{1-6}$alk-C(O)-aryl substituted by diazirinyl such as

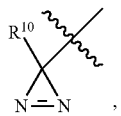

wherein $R^{10}$ is H, $C_{1-6}$alkyl, or halogenated $C_{1-6}$alkyl.

Aspect 28: The compound of aspect 26 or 27, wherein $R^{10}$ is H.

Aspect 29: The compound of aspect 26 or 27, wherein $R^{10}$ is $C_{1-6}$alkyl such as methyl, ethyl, propyl, butyl, pentyl, or hexyl.

Aspect 30: The compound of any one of the preceding aspects, wherein $R^4$ is H.

Aspect 31: The compound of any one of the preceding aspects, wherein $R^4$ is Br, Cl, or F, preferably F.

Aspect 32: The compound of any one of the preceding aspects, wherein $R^5$ is H;

Aspect 33: The compound of any one of the preceding aspects, wherein $R^5$ is Br, Cl, or F, preferably F.

Aspect 34: The compound of aspect 1, which is of formula (IA):

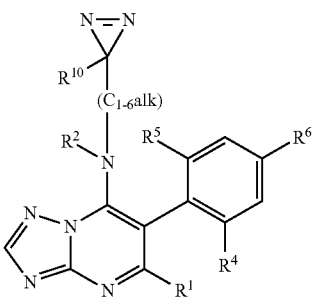

wherein, $R^{10}$ is H, $C_{1-6}$alkyl, or halogenated $C_{1-6}$alkyl.

Aspect 35: The compound of aspect 1, which is of formula (IB):

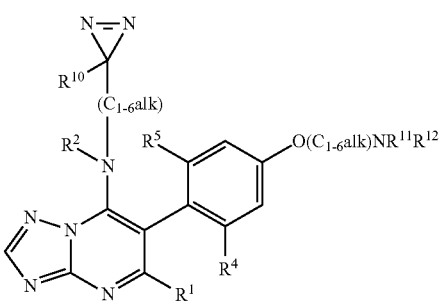

wherein:

$R^{10}$ is H, $C_{1-6}$alkyl, or halogenated $C_{1-6}$alkyl;

$R^{11}$ is H, $C_{1-6}$alkyl, or halogenated $C_{1-6}$alkyl; and $R^{12}$ is H, $C_{1-6}$alkyl, or halogenated $C_{1-6}$alkyl.

Aspect 36: The compound of aspect 1, which is of formula (IIA):

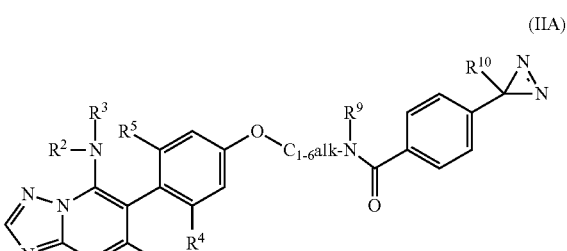

wherein:

$R^9$ is H, $C_{1-6}$alkyl, or substituted $C_{1-6}$alkyl; and $R^{10}$ is H, $C_{1-6}$alkyl, or halogenated $C_{1-6}$alkyl.

Aspect 37: The compound of aspect 1, that is:

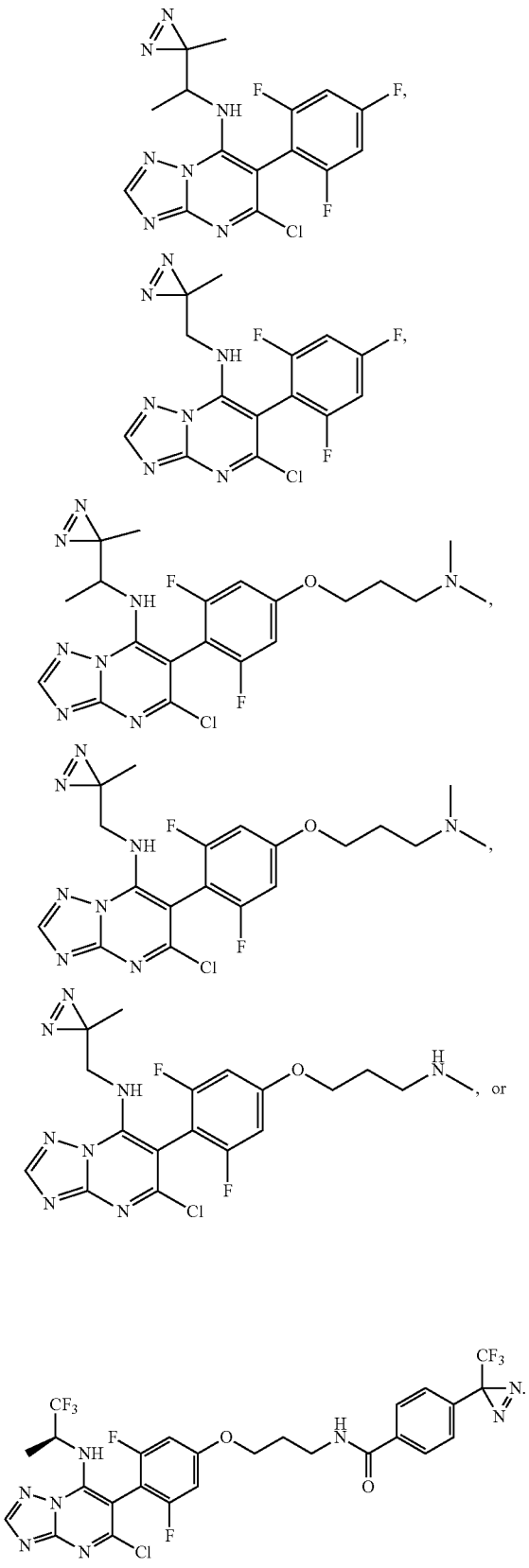

Aspect 38: The compound of aspect 1, that is:

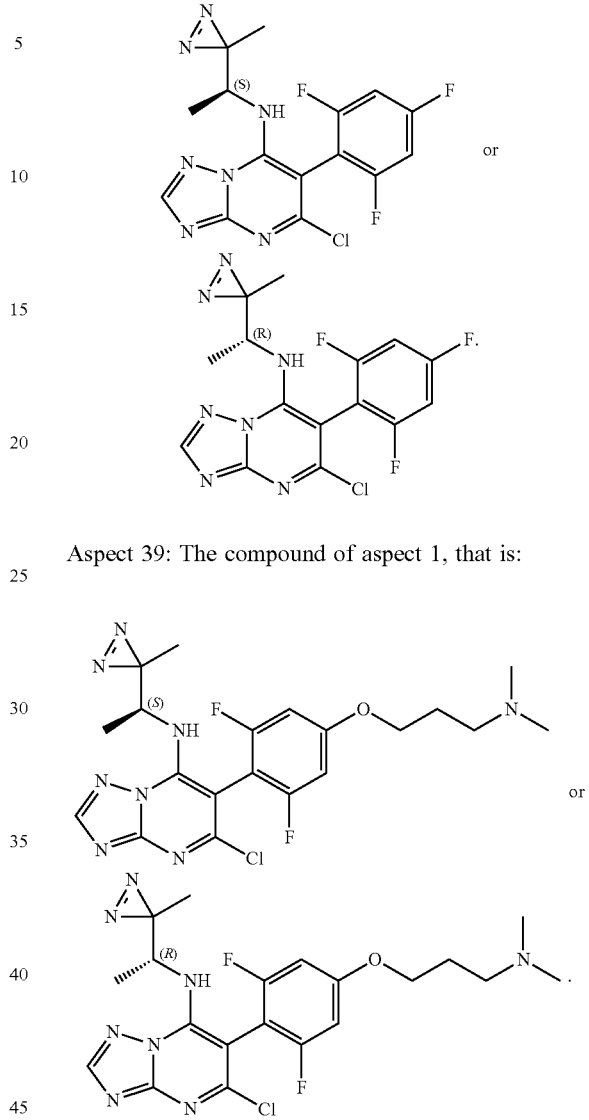

Aspect 39: The compound of aspect 1, that is:

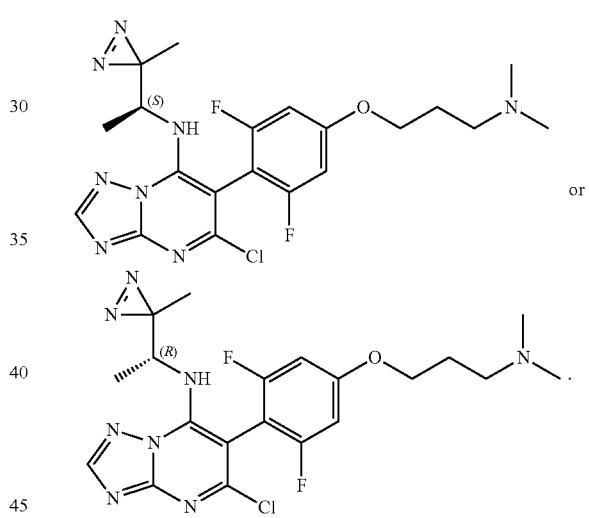

Aspect 40: A composition comprising a compound of any one of the preceding aspects and a pharmaceutically acceptable excipient.

Aspect 41: A method of stabilizing microtubules in a patient comprising administering to the patient a microtubule-stabilizing amount of a compound of any one of aspects 1 to 39.

Aspect 42: The method of aspect 41, wherein the patient has a disease that is a neurodegenerative disease or cancer.

Aspect 43: A method of treating a neurodegenerative disease in a patient comprising administering to the patient a therapeutically effective amount of a compound of any one of aspects 1 to 39.

Aspect 44: The method of aspect 43, wherein the neurodegenerative disease is characterized by a tauopathy or compromised microtubule function in the brain of the patient.

Aspect 45: The method of aspect 43 or 44, wherein the neurodegenerative disease is Alzheimer's disease, frontotemporal lobar degeneration, Pick's disease, progressive supranuclear palsy (PSP), corticobasal degeneration, Parkinson's disease (PD), PD with dementia, Lewy body disease with dementia, or amyotrophic lateral sclerosis.

Aspect 46: The method of aspect 43 or 44, wherein the neurodegenerative disease is traumatic brain injury, in particular, repetitive traumatic brain injury and chronic traumatic encephalopathy, or post-traumatic stress disorder.

Aspect 47: The method of aspect 43 or 44, wherein the neurodegenerative disease is schizophrenia.

Aspect 48: A method of treating a cancer in a patient comprising administering to the patient a therapeutically effective amount of a compound of any one of aspects 1 to 39.

Aspect 49: The method of aspect 48, wherein the cancer is breast cancer, uterine cancer, lung cancer, ovarian cancer, and skin cancer, or non-Hodgkin's lymphoma.

EXAMPLES

Example 1: 5-chloro-7-(1S,3R)-3-methoxy-8-azabicyclo[3.2.1]octan-8-yl)-6-(2,4,6-trifluorophenyl)-[1,2,4]triazolo[1,5-a]pyrimidine (2)

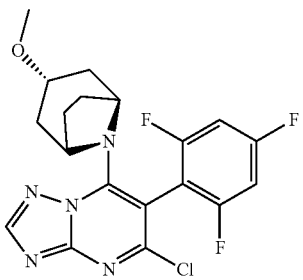

To a stirred solution of 5,7-dichloro-6-(2,4,6-trifluorophenyl)-[1,2,4]triazolo[1,5-a]pyrimidine 9 (50 mg, 0.16 mmol, 1.00 equiv) in anhydrous DMF (5.10 mL) was added endo-3-Methoxy-8-azabicyclo[3.2.1]octane hydrochloride (31 mg, 0.17 mmol, 1.10 equiv) and DIPEA (82 µL, 0.47 mmol, 3.00 equiv). After 1.5 h at r.t. the reaction was quenched with water and extracted with EtOAc (3×). The combined organic layer was washed with water, brine, dried over $MgSO_4$ and concentrated. The crude product was purified by silica gel column chromatography (0-30% of EtOAc in Hexanes) to give the desired product (38 mg, 0.09 mmol) as white solid. $^1$H NMR (600 MHz, $CDCl_3$) δ 8.28 (s, 1H), 6.83 (t, J=7.9 Hz, 2H), 4.61 (s, 2H), 3.45 (t, J=4.4 Hz, 1H), 3.23 (s, 3H), 2.14-2.09 (m, 2H), 2.05-1.99 (m, 2H), 1.93-1.93 (m, 2H), 1.81-1.76 (m, 2H). HRMS (ES+) calculated for $C_{19}H_{18}ClF_3N_5O$ [M+H]$^+$ 424.1146, found 424.1145. IR (KBr) v 2926, 1636, 1594, 1534, 1454, 1324, 1534, 1260, 1235, 1126, 1091, 1032, 999, 955, 736, 654, 538, 512 cm$^{-1}$.

Example 2: (S)—N-(3-(4-(5-chloro-7-((1,1,1-trifluoropropan-2-yl)amino)-[1,2,4]triazolo[1,5-a]pyrimidin-6-yl)-3,5-difluorophenoxy)propyl)-4-(3-(trifluoromethyl)-3H-diazirin-3-yl)benzamide (11)

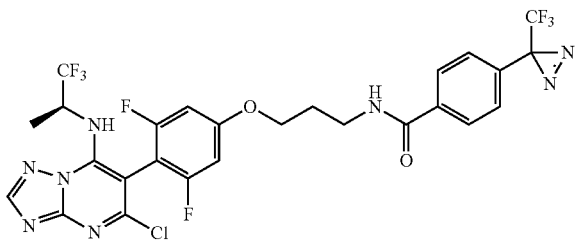 [SMILES: C[C@H](Nc1c(-c2c(F)cc(OCCCNC(=O)c3ccc(C4(C(F)(F)F)N=N4)cc3)cc2F)c(Cl)nc2ncnn12)C(F)(F)F]

To a solution of 4-(3-(trifluoromethyl)-3H-diazirin-3-yl)benzoic acid (7.7 mg, 0.033 mmol) in dichloromethane (0.07 mL) at 0° C., was added 1,1'-carbonyldiimidazole (5.4 mg, 0.033 mmol). The reaction mixture was stirred at 0° C. for 1 h, then transferred via cannula to a solution of (S)-6-(4-(3-aminopropoxy)-2,6-difluorophenyl)-5-chloro-N-(1,1,1-trifluoropropan-2-yl)-[1,2,4]triazolo[1,5-a]pyrimidin-7-amine 12 (22.5 mg, 0.05 mmol) (in dichloromethane (0.1 mL). The reaction mixture was stirred at room temperature for 21 h, then the solvent was evaporated and the crude products were purified by reverse-phase HPLC to afford the title compound as a white solid (5.8 mg, 27% yield). $^1$H-NMR (500 MHz; MeOD): δ 8.74 (t, J=5.2 Hz, 1H), 8.49 (s, 1H), 7.92 (d, J=8.6 Hz, 2H), 7.35 (d, J=8.2 Hz, 2H), 6.81 (dd, J=9.3, 2.1 Hz, 2H), 4.18 (t, J=6.0 Hz, 2H), 3.61 (q, J=6.2 Hz, 2H), 2.15 (quintet, J=6.4 Hz, 2H), 1.45 (d, J=6.9 Hz, 3H). $^{13}$C-NMR (126 MHz; $CDCl_3$): δ 166.71, 162.70 (dd, J=33.7, 8.8 Hz), 162.44 (t, J=13.8 Hz), 160.71 (dd, J=32.3, 8.8 Hz), 158.59, 155.35, 146.13, 135.57, 132.75, 127.48, 126.90, 124.44 (dd, J=278.2, 53.4 Hz), 121.29, 120.95, 101.01 (t, J=20.9 Hz), 99.33 (ddd, J=34.5, 25.5, 3.1 Hz), 92.51, 67.31, 50.90 (q, J=32.1 Hz), 37.75, 29.23, 28.49 (q, J=40.7 Hz), 15.34. HRMS (ESI+) calculated for $C_{26}H_{19}ClF_8N_8O_2Na$ [M+Na$^+$]: 685.1089, found 685.1102. IR (KBr) v 2940, 2877, 1646, 1617, 1575, 1552, 1184, 1156 cm$^{-1}$.

Example 3: Intermediate Compounds 4-6

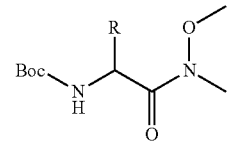

4 R = (S)-$CH_3$
5 R = (R)-$CH_3$
6 R = H

These compounds were prepared using the procedure of *J. Am. Chem. Soc.*, 1999, 121 (13): 2974-2986. To a stirred solution of the corresponding Boc-protected amino acid (Boc-D-Ala-OH, Boc-L-Ala-OH or Boc-Gly-OH) (1.00 equiv) in anhydrous dichloromethane (0.3 M) at 0° C. was added 1,1'-carbonyldiimidazole (1.40 equiv). After 30 min at 0° C., Et₃N (1.40 equiv) and N,O-dimethylhydroxylamine (1.40 equiv) were added. After 30 min, the reaction was stirred at r.t overnight. Et₂O (for each 1.00 mmol of protected amino acid, add 6.70 mL of Et₂O) was added and the organic layer was washed (×3) with a solution of HCl (1N) (for each 1.00 mmol of protected amino acid, wash with 2.50 mL of HCl 1N), saturated solution of NaHCO₃, brine and dried over MgSO₄, filtered and concentrated to give the desired product as white solid yield without furthermore purification.

Example 4: tert-butyl (S)-(1-(methoxy(methyl) amino)-1-oxopropan-2-yl)carbamate (17a)

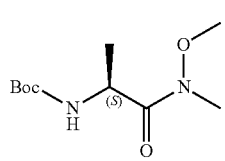

17a

Following the general procedure A using Boc-L-Ala-OH (3.00 g, 15.86 mmol) provide the desired product as white solid (3.34 g, 14.38 mmol) in 91% yield. ¹H NMR (600 MHz, CDCl₃) δ 5.25 (d, J=6.3 Hz, 1H), 4.68 (s, 1H), 3.77 (s, 3H), 3.21 (s, 3H), 1.43 (s, 9H), 1.31 (d, J=6.9 Hz, 3H). ¹³C NMR (151 MHz, CDCl₃) δ 173.77, 155.30, 79.61, 61.75, 46.63, 32.23, 28.48, 18.80. HRMS (ES+) calculated for $C_{10}H_{20}N_2NaO_4$ [M+Na]⁺ 255.1321, found 255.1316. IR (KBr) v 3299, 2973, 1704, 1660, 1548, 1455, 1362, 1177, 1066, 981, 570 cm⁻¹.

Example 5: tert-butyl (R)-(1-(methoxy(methyl) amino)-1-oxopropan-2-yl)carbamate (18a)

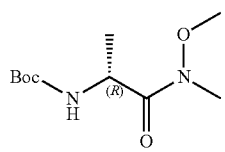

18a

Following the general procedure A using Boc-D-Ala-OH (3.00 g, 15.86 mmol) provide the desired product as white solid (3.27 g, 14.08 mmol) in 89%. ¹H NMR (600 MHz, CDCl₃) δ 5.25 (d, J=5.3 Hz, 1H), 4.66 (s, 1H), 3.75 (s, 3H), 3.19 (s, 3H), 1.42 (s, 9H), 1.29 (d, J=7.0 Hz, 3H). ¹³C NMR (151 MHz, CDCl₃) δ 173.77, 155.30, 79.62, 61.75, 46.63, 32.23, 28.48, 18.78. HRMS (ES+) calculated for $C_{10}H_{20}N_2NaO_4$ [M+Na]⁺ 255.1321, found 255.1317. IR (KBr) v 3241, 1704, 1660, 1362, 1066, 981, 788, 570 cm⁻¹.

Example 6: tert-butyl (2-(methoxy(methyl)amino)-2-oxoethyl)carbamate (19a)

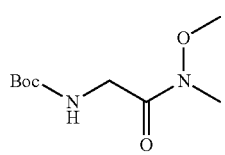

19a

Following the general procedure A using Boc-Gly-OH (5.00 g, 28.54 mmol) provide the desired product as white solid (5.65 g, 25.89 mmol) in 91% yield. ¹H NMR (600 MHz, CDCl₃) δ 5.27 (s, 1H), 4.06 (s, 2H), 3.69 (s, 3H), 3.18 (s, 3H), 1.43 (s, 9H). ¹³C NMR (151 MHz, CDCl₃) δ 170.30, 155.99, 79.73, 61.56, 41.80, 32.45, 28.43. HRMS (ES+) calculated for $C_9H_{18}N_2NaO_4$ [M+Na]⁺ 241.1164, found 241.1161. IR (KBr) v 3266, 2974, 1716, 166, 1439, 1264, 1170, 1050, 986, 867, 743, 612, 488 cm⁻¹.

Example 7: Preparation of Compounds 7-9 Via General Procedure B

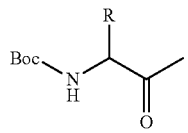

7 R = (S)-CH₃
8 R = (R)-CH₃
9 R = H

These compounds were prepared using a modified procedure of *J. Am. Chem. Soc.*, 1999, 121 (13), pp 2974-2986. To a solution of Weinreb amide 17a, 18a or 19a (1.00 equiv) in anhydrous THF (0.25 M) at −78° C. was dropwise added MeLi ([C]=2.2 M in Et₂O, 3.00 equiv). After 2 h at −78° C. the reaction was quenched with a saturated solution of NH₄Cl. Water was added and extracted (3×) with EtOAc. The combined organic layers was washed with brine, dried over MgSO₄, filtrated and concentrated. The crude product was purified by silica gel column chromatography to give the desired product.

Example 8: tert-butyl (S)-(3-oxobutan-2-yl)carbamate (17b)

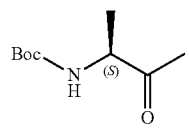

17b

Following the general procedure B using tert-butyl (S)-(1-(methoxy(methyl)amino)-1-oxopropan-2-yl)carbamate 17a (3.30 g, 14.21 mmol) provide after purification by silica column chromatography (0-20% of EtOAc in Hexanes) the desired product as a pale yellow solid (1.74 g, 9.29 mmol) in 66% yield. ¹H NMR (600 MHz, CDCl₃) δ 5.28 (s, 1H), 4.29 (p, J=6.9 Hz, 1H), 2.19 (s, 3H), 1.42 (s, 9H), 1.32 (d, J=7.2 Hz, 3H). ¹³C NMR (151 MHz, CDCl₃) δ 207.55, 155.30, 79.83, 55.75, 28.43, 26.58, 17.76. HRMS (ES+) calculated for $C_9H_{17}NNaO_3$ [M+Na]⁺ 210.1106, found 210.1102. IR (KBr) v 3309, 2978, 2934, 1711, 1512, 1457, 1366, 1292, 1249, 1173, 1071, 1021, 865, 782, 617 cm⁻¹.

Example 9: tert-butyl (R)-(3-oxobutan-2-yl)carbamate (18b)

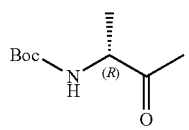

Following the general procedure B using tert-butyl (R)-(1-(methoxy(methyl)amino)-1-oxopropan-2-yl)carbamate 18a (2.50 g, 10.76 mmol) provide after purification by silica column chromatography (0-20% of EtOAc in Hexanes) the desired product as a pale yellow solid (1.26 g, 6.75 mmol) in 63% yield. $^1$H NMR (600 MHz, CDCl$_3$) δ 5.28 (s, 1H), 4.28 (p, J=6.4 Hz, 1H), 2.18 (s, 3H), 1.41 (s, 9H), 1.32 (d, J=7.2 Hz, 3H). $^{13}$C NMR (151 MHz, CDCl$_3$) δ 207.52, 155.28, 79.79, 55.74, 28.42, 26.56, 17.74. HRMS (ES+) calculated for C$_9$H$_{17}$NNaO$_3$ [M+Na]$^+$ 210.1106, found 210.1102. IR (KBr) ν 3354, 2981, 2935, 1560, 1509, 1367, 1293, 1250, 1172, 1072, 865, 782, 617 cm$^{-1}$.

Example 10: tert-butyl (2-oxopropyl)carbamate (19b)

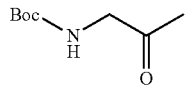

Following the general procedure B using tert-butyl (2-(methoxy(methyl)amino)-2-oxoethyl)carbamate 19a (5.50 g, 25.20 mmol) provide after purification by silica column chromatography (0-40% of EtOAc in Hexanes) the desired product as a limpid yellow oil (3.75 g, 21.65 mmol) in 86% yield. $^1$H NMR (600 MHz, CDCl$_3$) δ 5.23 (s, 1H), 4.01 (d, J=4.9 Hz, 2H), 2.20-2.11 (m, 3H), 1.42 (d, J=8.5 Hz, 9H). $^{13}$C NMR (151 MHz, CDCl$_3$) δ 203.54, 155.69, 79.94, 51.03, 28.41, 27.24. HRMS (ES+) calculated for C$_8$H$_{15}$NNaO$_3$ [M+Na]$^+$ 196.0950, found 196.0945. IR (KBr) ν 3383, 2979, 2933, 1711, 1521, 1367, 1285, 1251, 1166, 1083, 965, 884, 781, 522 cm$^{-1}$.

Example 11: Preparation of Compounds 10-12 by General Procedure C

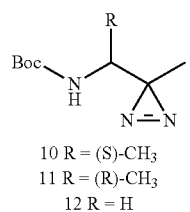

10 R = (S)-CH$_3$
11 R = (R)-CH$_3$
12 R = H

These compounds were prepared via a modification of *J. Am. Chem. Soc.*, 2014, 136 (30), pp 10777-10782. To a solution of ketone 17b, 18b or 19b (1.00 equiv) in anhydrous MeOH (5.00 M) at 0° C. was slowly added a solution of ammonium (7 N in MeOH, 1 mL per mmol of ketone). After 3 h at 0° C., a suspension hydroxylamine-O-sulfonic acid (1.1 equiv) in anhydrous MeOH (11.0 M) was added. The reaction was stirred at r.t. overnight. The mixture was concentrated and anhydrous MeOH was added. The suspension was filtered and the filtrate was concentrated. Anhydrous MeOH (1.40 M) was added and cooled down 0° C. Anhydrous Et$_3$N (1.60 equiv) was added follow by a portionwise addition of I$_2$ (0.40 equiv)). After 10 min at 0° C., the reaction was diluted with EtOAc. The organic layer was washed with a HCl solution (1N), an aqueous solution of Na$_2$S$_2$O$_3$ (10% wt), dried over Na$_2$SO$_4$, filtered and concentrated. The crude product was purified by silica gel column chromatography to give the desired compound.

Example 12: tert-butyl (S)-(1-(3-methyl-3H-diazirin-3-yl)ethyl)carbamate (17c)

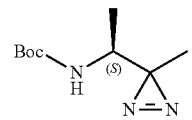

Following the general procedure C using tert-butyl (S)-(3-oxobutan-2-yl)carbamate 17b (1.70 g, 9.08 mmol) provide after purification by silica column chromatography (0-10% of EtOAc in hexanes) the desired product as limpid yellow oil (427 mg, 2.14 mmol) in 24% yield. $^1$H NMR (600 MHz, CDCl$_3$) δ 4.20 (s, 1H), 3.88-3.78 (m, 1H), 1.44 (s, 9H), 1.04 (s, 3H), 0.83 (d, J=6.4 Hz, 3H). $^{13}$C NMR (151 MHz, CDCl$_3$) δ 155.15, 79.89, 48.51, 28.78, 28.45, 17.79, 16.42. HRMS (ES+) calculated for C$_9$F$_{17}$N$_3$NaO$_2$ [M+Na]$^+$ 222.1218, found 222.1212. IR (KBr) ν 3319, 2979, 2934, 1698, 1455, 1366, 1249, 1174, 1074, 1048, 860, 781, 461 cm$^{-1}$.

Example 13: tert-butyl (R)-(1-(3-methyl-3H-diazirin-3-yl)ethyl)carbamate (18c)

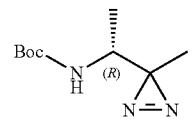

Following the general procedure C using tert-butyl (R)-(3-oxobutan-2-yl)carbamate 18b (920 mg, 4.91 mmol) provide after purification by silica column chromatography (0-10% of EtOAc in hexanes) the desired product as limpid yellow oil (127 mg, 0.64 mmol) in 13% yield. $^1$H NMR (600 MHz, CDCl$_3$) δ 4.41 (s, 1H), 3.74 (s, 1H), 1.35 (s, 9H), 0.95 (s, 3H), 0.75 (d, J=6.5 Hz, 3H). $^{13}$C NMR (151 MHz, CDCl$_3$) δ 155.09, 79.55, 48.34, 28.64, 28.29, 17.60, 16.17. HRMS (ES+) calculated for C$_9$F$_{17}$N$_3$NaO$_2$ [M+Na]$^+$ 222.1218, found 222.1212. IR (KBr) ν 3355, 2980, 2932, 1701, 1542, 1367, 1249, 1174, 1074, 1048, 860, 782 cm$^{-1}$.

Example 14: tert-butyl ((3-methyl-3H-diazirin-3-yl)methyl)carbamate (19c)

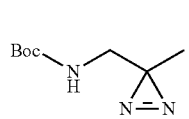

19c

Following the general procedure C using tert-butyl (2-oxopropyl)carbamate 19b (2.00 g, 11.50 mmol) provide after purification by silica column chromatography (0-10% of EtOAc in hexanes) the desired product as limpid colorless oil (788 mg, 4.25 mmol) in 37% yield. $^1$H NMR (600 MHz, CDCl$_3$) δ 4.40 (s, 1H), 3.11 (d, J=5.7 Hz, 2H), 1.42 (s, 9H), 1.05 (s, 3H). $^{13}$C NMR (151 MHz, CDCl$_3$) δ 155.75, 80.03, 44.04, 28.42, 25.78, 17.95. HRMS (ES+) calculated for C$_8$H$_{15}$N$_3$NaO$_2$[M+Na]$^+$ 208.1062, found 208.1058. IR (KBr) ν 3337, 2980, 2932, 1697, 1511, 1367, 1392, 1253, 1172, 1040, 1013, 932, 862, 782, 654 cm$^{-1}$.

Example 15: Preparation of Compounds 17-19 by General Procedure D

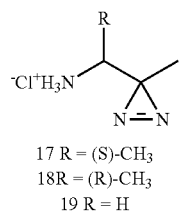

17 R = (S)-CH$_3$
18 R = (R)-CH$_3$
19 R = H

These compounds were prepared using a modified version of *J. Am. Chem. Soc.*, 2014, 136 (30), pp 10777-10782. To a solution of protected amine 17c, 18c, 19c (1.00 equiv) in MeOH (1.1 M) at 0° C. in a dark was slowly added a solution of HCl ([C]=4 N in 1,4-dioxane, 920 μL for each mmol of protected amine). After 30 min. at 0° C., the reaction was stirred 30 min. at r.t. The reaction was concentrated to give a solid which was filtered and washed with Et$_2$O to give the desired compound without further purification.

Example 16: (S)-1-(3-methyl-3H-diazirin-3-yl)ethanamine hydrochloride (17)

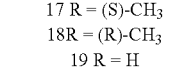

17

Following the general procedure D using tert-butyl (S)-(1-(3-methyl-3H-diazirin-3-yl)ethyl)carbamate 17c (100 mg, 0.50 mmol) provide the desired product as white solid (65 mg, 0.48 mmol) in 95% yield. $^1$H NMR (600 MHz, MeOD) δ 3.35-3.32 (m, 1H), 1.15 (s, 3H), 1.07 (d, J=7.0 Hz, 3H). $^{13}$C NMR (151 MHz, MeOD) δ 51.79, 27.13, 16.71, 14.79. HRMS (ES+) calculated for C$_4$H$_{10}$N$_3$ [M+H]$^+$ 100.0869, found 100.0869.

Example 17: (R)-1-(3-methyl-3H-diazirin-3-yl)ethanamine hydrochloride (18)

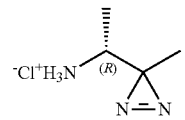

18

Following the general procedure D using tert-butyl (R)-(1-(3-methyl-3H-diazirin-3-yl)ethyl)carbamate 18c (120 mg, 0.60 mmol) provide the desired product as white solid (78 mg, 0.58 mmol) in 96% yield. $^1$H NMR (600 MHz, MeOD) δ 3.34 (q, J=6.9 Hz, 1H), 1.16 (s, 3H), 1.07 (d, J=6.9 Hz, 3H). $^{13}$C NMR (151 MHz, MeOD) δ 51.80, 27.14, 16.75, 14.80. HRMS (ES+) calculated for C$_4$H$_{10}$N$_3$ [M+H]$^+$ 100.0869, found 100.0867.

Example 18: (3-methyl-3H-diazirin-3-yl)methanamine hydrochloride (19)

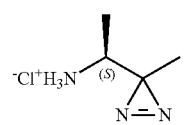

19

Following the general procedure D using tert-butyl ((3-methyl-3H-diazirin-3-yl)methyl)carbamate 19c (120 mg, 0.65 mmol) provide the desired product as white solid (72 mg, 0.59 mmol) in 91% yield. $^1$H NMR (600 MHz, MeOD) δ 2.92 (s, 2H), 1.19 (s, 3H). $^{13}$C NMR (151 MHz, MeOD) δ 45.21, 24.15, 17.89. HRMS (ES+) calculated for C$_3$H$_8$N$_3$ [M+H]$^+$ 86.0713, found 86.0717.

Example 19: Preparation of Compounds 14-17 Via General Procedure E

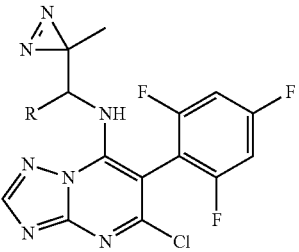

14 R = (S)-CH$_3$
15 R = (R)-CH$_3$
16 R = H

To a stirred solution of 5,7-dichloro-6-(2,4,6-trifluorophenyl)-[1,2,4]triazolo[1,5-a]pyrimidine 6 (1.00 equiv) in anhydrous DMF (0.14 M) in the dark was added Et$_3$N (3.00 equiv) and the desired amine 17, 18 or 19 (1.10 equiv). After 1 h at r.t., water was added and extracted with EtOAc (×3). The combined organic layer was washed with water, brine, dried over MgSO$_4$ and concentrated. The crude product was purified by silica gel column chromatography to give the desired compound.

Example 20: (S)-5-chloro-N-(1-(3-methyl-3H-diazirin-3-yl)ethyl)-6-(2,4,6-trifluorophenyl)-[1,2,4]triazolo[1,5-a]pyrimidin-7-amine (14)

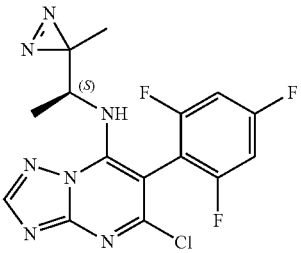

14

Following the general procedure E using 5,7-dichloro-6-(2,4,6-trifluorophenyl)-[1,2,4]triazolo[1,5-a]pyrimidine 9 (64 mg, 0.20 mmol) and (S)-1-(3-methyl-3H-diazirin-3-yl)ethanamine hydrochloride 17 (30 mg, 0.22 mmol) provide after purification by silica column chromatography (0-40% of EtOAc in hexanes) the desired product as white foam (57 mg, 0.15 mmol) in 74% yield. $^1$H NMR (600 MHz, CDCl$_3$) δ 8.34 (s, 1H), 6.94-6.81 (m, 2H), 5.93 (d, J=8.4 Hz, 1H), 3.91 (s, 1H), 0.93 (d, J=6.8 Hz, 3H), 0.89 (s, 3H). $^{13}$C NMR (151 MHz, CDCl$_3$) δ 164.25 (dt, J=254.7, 15.2 Hz), 161.65 (ddd, J=252.2, 15.0, 8.4 Hz), 161.46 (ddd, J=250.9, 14.9, 8.2 Hz), 158.00, 155.17, 153.85, 145.90, 106.34 (td, J=20.7, 4.7 Hz), 101.37 (dtd, J=40.3, 25.9, 4.0 Hz), 90.15, 52.05, 28.18, 17.61, 16.96. HRMS (ES+) calculated for C$_{15}$H$_{12}$ClF$_3$N$_7$ [M+H]$^+$ 382.0789, found 382.0791. IR (KBr) ν 3333, 1615, 1560, 1360, 1249, 1208, 1123, 1037, 999, 964, 845, 766, 738 cm$^{-1}$.

Example 21: (R)-5-chloro-N-(1-(3-methyl-3H-diazirin-3-yl)ethyl)-6-(2,4,6-trifluorophenyl)-[1,2,4]triazolo[1,5-a]pyrimidin-7-amine (15)

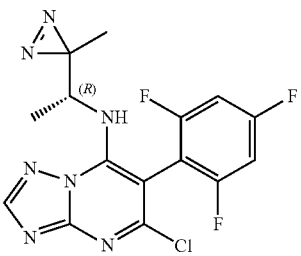

15

Following the general procedure E using 5,7-dichloro-6-(2,4,6-trifluorophenyl)-[1,2,4]triazolo[1,5-a]pyrimidine 9 (65 mg, 0.20 mmol) and (R)-1-(3-methyl-3H-diazirin-3-yl)ethanamine hydrochloride 18 (31 mg, 0.22 mmol) provide after purification by silica column chromatography (0-40% of EtOAc in hexanes) the desired product as white foam (58 mg, 0.15 mmol) in 75% yield. $^1$H NMR (600 MHz, CDCl$_3$) δ 8.34 (s, 1H), 6.99-6.82 (m, 2H), 5.93 (d, J=8.2 Hz, 1H), 3.91 (s, 1H), 0.93 (d, J=6.8 Hz, 3H), 0.88 (s, 3H). $^{13}$C NMR (151 MHz, CDCl$_3$) δ 164.24 (dt, J=254.7, 15.2 Hz), 161.64 (ddd, J=252.2, 14.9, 8.4 Hz), 161.45 (ddd, J=251.0, 14.9, 8.3 Hz), 157.99, 155.16, 153.85, 145.90, 106.33 (td, J=20.8, 4.7 Hz), 101.36 (dtd, J=40.2, 25.9, 4.0 Hz), 90.15, 52.05, 28.18, 17.60, 16.96. HRMS (ES+) calculated for C$_{15}$H$_{12}$ClF$_3$N$_7$ [M+H]$^+$ 382.0789, found 382.0792. IR (KBr) ν 3227, 1613, 1562, 1493, 1457, 1361, 1249, 1207, 1123, 1037, 999, 964, 845, 766 cm$^{-1}$.

Example 22: 5-chloro-N-((3-methyl-3H-diazirin-3-yl)methyl)-6-(2,4,6-trifluorophenyl)-[1,2,4]triazolo[1,5-a]pyrimidin-7-amine (16)

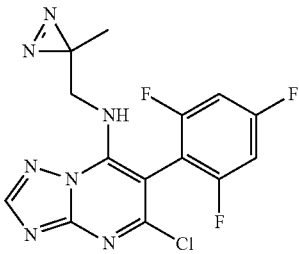

16

Following the general procedure E using 5,7-dichloro-6-(2,4,6-trifluorophenyl)-[1,2,4]triazolo[1,5-a]pyrimidine 9 (89 mg, 0.28 mmol) and (3-methyl-3H-diazirin-3-yl)methanamine hydrochloride 19 (37 mg, 0.31 mmol) provide after purification by silica column chromatography (0-50% of EtOAc in Hexanes) the desired product as white foam (57 mg, 0.16 mmol) in 56% yield. $^1$H NMR (600 MHz, CDCl$_3$) δ 8.39 (s, 1H), 6.88 (t, J=7.7 Hz, 2H), 6.28 (s, 1H), 3.35 (d, J=4.5 Hz, 2H), 0.99 (s, 3H). HRMS (ES+) calculated for C$_{14}$H$_9$ClF$_3$N$_7$Na [M+Na]$^+$ 390.0452, found 390.0454. IR (KBr) ν 3379, 1617, 1571, 1498, 1253, 1124, 1037, 999, 845, 767 cm$^{-1}$.

Example 23: Preparation of Compounds 20-22 Via General Procedure F

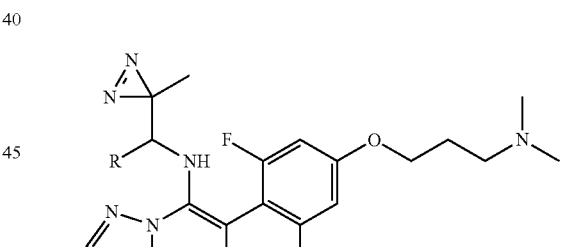

20 R = (S)-CH$_3$
21 R = (R)-CH$_3$
22 R = H

To a suspension of NaH (60 wt % in mineral oil) (4.00 equiv) in a mixture of anhydrous DMSO/THF (2:1, C=0.35 M (from NaH)) was added 3-(dimethylamino)propan-1-ol (4.00 equiv). The reaction was stirred at 60° C. for 1 h. Then, a solution of the corresponding triazolopyrimidine 14, 15 or 16 in mixture of anhydrous DMSO/THF (1:1, C=0.52 M from triazolopyrimidine) was added at 60° C. and stirred for 3 h in the dark. After that, a further addition of 3-(dimethylamino)propan-1-ol (4.00 equiv) and NaH (60 wt % in mineral oil) (4.00 equiv) was carried out and the reaction was stirred at 60° C. overnight. The reaction was quenched at r.t with water and extracted (3×) with EtOAc. The combined organic layer was washed with brine, dried over MgSO$_4$ and concentrated. The crude product was purified by reverse-phase HPLC to provide the formic acid salt of the desired compound.

Example 24: (S)-5-chloro-6-(4-(3-(dimethylamino)propoxy)-2,6-difluorophenyl)-N-(1-(3-methyl-3H-diazirin-3-yl)ethyl)-[1,2,4]triazolo[1,5-a]pyrimidin-7-amine (20)

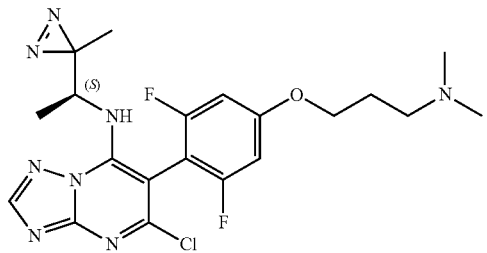

Following the general procedure F using (S)-5-chloro-N-(1-(3-methyl-3H-diazirin-3-yl)ethyl)-6-(2,4,6-trifluorophenyl)-[1,2,4]triazolo[1,5-a]pyrimidin-7-amine 14 (50 mg, 0.13 mmol) provide after purification by reverse-phase HPLC the formic acid salt of the desired compound as a white solid (13 mg, 0.03 mmol) in 20% yield. $^1$H NMR (600 MHz, CDCl$_3$) δ 8.35 (s, 1H), 6.67-6.62 (m, 2H), 5.87 (s, 1H), 4.10 (t, J=5.9 Hz, 2H), 3.99 (s, 1H), 2.59 (t, J=6.8 Hz, 2H), 2.36 (s, 6H), 2.15-2.03 (m, 2H), 0.90 (s, 3H), 0.86 (d, J=6.7 Hz, 3H). $^{13}$C NMR (151 MHz, CDCl$_3$) δ 168.51, 162.38 (t, J=15.1 Hz), 161.81 (dd, J=248.6, 9.1 Hz), 161.45 (dd, J=248.6, 9.0 Hz), 158.65, 155.14, 153.82, 145.98, 101.59 (t, J=21.1 Hz), 99.13 (ddd, J=30.2, 25.7, 3.0 Hz), 91.15, 67.13, 55.92, 51.83, 45.20, 28.28, 26.81, 17.79, 17.16. HRMS (ES+) calculated for C$_{20}$H$_{24}$ClF$_2$N$_8$O [M+H]$^+$ 465.1724, found 465.1727. IR (KBr) ν 3334, 2954, 2819, 1541, 1455, 1355, 1247, 1206, 1156, 1099, 1034, 962, 841, 767, 736, 654, 546 cm$^{-1}$.

Example 25: (R)-5-chloro-6-(4-(3-(dimethylamino)propoxy)-2,6-difluorophenyl)-N-(1-(3-methyl-3H-diazirin-3-yl)ethyl)-[1,2,4]triazolo[1,5-a]pyrimidin-7-amine (21)

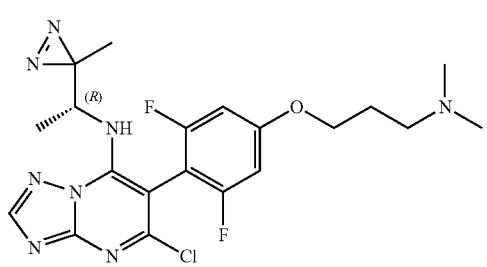

Following the general procedure F using (R)-5-chloro-N-(1-(3-methyl-3H-diazirin-3-yl)ethyl)-6-(2,4,6-trifluorophenyl)-[1,2,4]triazolo[1,5-a]pyrimidin-7-amine 15 (50 mg, 0.13 mmol) provide after purification by reverse-phase HPLC the formic acid salt of the desired compound as a white solid (49 mg, 0.09 mmol) in 74% yield. $^1$H NMR (600 MHz, CDCl$_3$) δ 8.32 (s, 1H), 6.63 (dd, J=19.4, 10.2 Hz, 2H), 5.88 (s, 1H), 4.09 (s, 2H), 3.98 (s, 1H), 2.67 (s, 2H), 2.40 (s, 6H), 2.09 (s, 2H), 0.88 (s, 3H), 0.86 (d, J=4.2 Hz, 3H). $^{13}$C NMR (151 MHz, CDCl$_3$) δ 168.46, 162.24 (t, J=13.9 Hz), 161.77 (dd, J=248.7, 9.0 Hz), 161.64 (dd, J=247.7, 9.0 Hz), 158.56, 155.08, 153.79, 145.98, 101.61 (t, J=21.1 Hz), 99.10 (ddd, J=30.9, 25.6, 2.9 Hz), 91.10, 66.94, 55.67, 51.80, 44.76, 28.27, 26.38, 17.72, 17.12. HRMS (ES+) calculated for C$_{20}$H$_{24}$ClF$_2$N$_8$O [M+H]$^+$ 465.1724, found 465.1727. IR (KBr) ν 2952, 2820, 2775, 1618, 1502, 1355, 1248, 1206, 1155, 1100, 1033, 963, 841, 767, 736, 654, 546 cm$^{-1}$.

Example 26: 5-chloro-6-(4-(3-(dimethylamino)propoxy)-2,6-difluorophenyl)-N-((3-methyl-3H-diazirin-3-yl)methyl)-[1,2,4]triazolo[1,5-a]pyrimidin-7-amine (22)

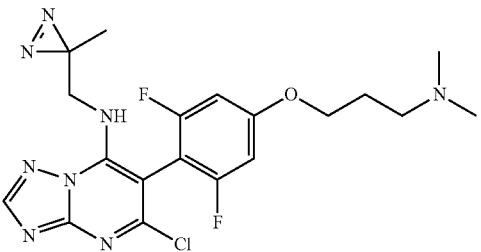

Following the general procedure F using 5-chloro-N-((3-methyl-3H-diazirin-3-yl)methyl)-6-(2,4,6-trifluorophenyl)-[1,2,4]triazolo[1,5-a]pyrimidin-7-amine 16 (40 mg, 0.11 mmol) provide after purification by reverse-phase HPLC the formic acid salt of the desired compound as a white solid (34.0 mg, 0.08 mmol) in 63% yield. $^1$H NMR (600 MHz, MeOD) δ 8.44 (s, 1H), 6.82 (d, J=9.4 Hz, 2H), 4.17 (t, J=5.6 Hz, 2H), 3.79 (s, 2H), 2.96 (t, J=12.0 Hz, 2H), 2.63 (s, 6H), 2.20-2.09 (m, 2H), 0.92 (s, 3H). $^{13}$C NMR (151 MHz, MeOD) δ 163.71 (t, J=14.2 Hz), 163.30 (dd, J=246.7, 9.3 Hz), 158.98, 155.92, 155.59, 149.47, 102.52 (t, J=21.3 Hz), 100.20 (dd, J=24.7, 4.2 Hz), 93.09, 67.71, 56.65, 46.83, 44.47, 27.02, 26.64, 17.52. HRMS (ES+) calculated for C$_{19}$H$_{22}$ClF$_2$N$_8$O [M+H]$^+$ 451.1568, found 451.1570. IR (KBr) ν 3252, 2956, 2820, 2773, 1611, 1577, 1508, 1354, 1252, 1206, 1153, 1032, 912, 842, 767, 736, 653, 587, 541 cm$^{-1}$.

Example 27: 5-chloro-6-(2,6-difluoro-4-(3-(methyl-amino)propoxy)phenyl)-N-((3-methyl-3H-diazirin-3-yl)methyl)-[1,2,4]triazolo[1,5-a]pyrimidin-7-amine (23)

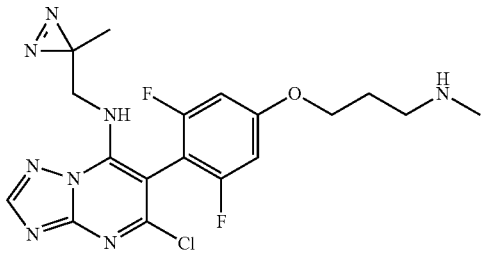

To a suspension of NaH (60 wt % in mineral oil) (66 mg, 1.64 mmol, 4.00 equiv) in a mixture of anhydrous DMSO/THF (2:1, 4.8 mL) was added 3-(methylamino)propan-1-ol (160 μL, 1.64 mmol, 4.00 equiv). The reaction was stirred at 60° C. for 1 h. Then, a solution of 5-chloro-N-((3-methyl-3H-diazirin-3-yl)methyl)-6-(2,4,6-trifluorophenyl)-[1,2,4]triazolo[1,5-a]pyrimidin-7-amine 16 (120 mg, 0.41 mmol, 1.00 equiv) in mixture of anhydrous DMSO/THF (1:1, 0.62 mL) was added at 60° C. and stirred for 3 h in the dark. The reaction was quenched at r.t with water and extracted (3×) with EtOAc. The combined organic layer was washed with water (×2), brine, dried over MgSO$_4$ and concentrated to give the desired compound (114 mg, 0.26 mmol) as yellow solid in 63% yield without furthermore purification. $^1$H NMR (600 MHz, CDCl$_3$) δ 8.26 (s, 1H), 6.52 (d, J=8.9 Hz, 2H), 5.02 (s, 2H), 4.03 (t, J=5.9 Hz, 2H), 3.55 (s, 2H), 2.83 (t, J=6.8 Hz, 2H), 2.48 (s, 3H), 2.06-2.00 (m, 2H), 0.94 (s, 3H). $^{13}$C NMR (151 MHz, CDCl$_3$) δ 162.03 (t, J=13.9 Hz), 161.78 (dd, J=248.2, 9.1 Hz), 158.16, 154.80, 154.09, 147.05, 101.27 (t, J=21.1 Hz), 98.88 (ddd, J=48.3, 28.7, 3.0 Hz), 91.50, 66.96, 48.18, 46.61, 35.98, 25.78, 17.51. HRMS (ES+) calculated for C$_{18}$H$_{20}$ClF$_2$N$_8$O [M+H]$^+$ 437.1411, found 437.1408. IR (KBr) ν 2928, 1614, 1576, 1508, 1355, 1252, 1207, 1153, 1038, 911, 840, 767, 737 cm$^{-1}$.

Example 28

The compounds where then evaluated in a cell-based MT assay as described in Kovalevich, Characterization of brain-penetrant pyrimidine-containing molecules with differential microtubule-stabilizing activities developed as potential therapeutic agents for Alzheimer's disease and related tauopathies. J. Pharmacol. Exp. Ther., 2016, 357, 432-50. In summary, acetylated α-tubulin and total α-tubulin levels were determined by ELISA in cell lysates after 4 h of incubation with test compound at either 1 or 10 μM. See, Table 1.

TABLE 1

| Compound | Acetylated α-Tubulin | | Total α-Tubulin | |
| --- | --- | --- | --- | --- |
| | 1 μM | 10 μM | 1 μM | 10 μM |
| Cevipabulin (1) | 7.07** ± 0.36 | 0.1** ± 0.01 | 0.51** ± 0.08 | 0.14** ± 0.03 |
| 5 | 5.83** ± 0.35 | 0.30** ± 0.15 | 0.29** ± 0.03 | 0.14** ± 0.01 |
| 2 | 3.65** ± 0.15 | 7.43** ± 0.93 | 1.12 ± 0.08 | 1.38** ± 0.19 |
| 3 | 2.78** ± 0.17 | 5.04** ± 0.45 | 1.18 ± 0.09 | 1.22 ± 0.18 |
| 4 | 2.14** ± 0.15 | 2.59** ± 0.15 | 1.10 ± 0.17 | 0.90 ± 0.16 |
| 6 | <10-15% increase | <10-15% increase | ND | ND |
| 8 | 0.97 ± 0.06 | 4.99** ± 0.27 | 0.74** ± 0.14 | 0.46** ± 0.06 |
| 7 | <10-15% increase | <10-15% increase | ND | ND |
| 11 | 1.30 ± 0.28 | 3.65** ± 0.74 | 1.31** ± 0.13 | 0.88 ± 0.05 |
| 14 | ND | 1.85** ± 0.08 | ND | 0.94 ± 0.02 |
| 20 | 6.7** ± 0.45 | 0.28* ± 0.03 | 0.69** ± 0.05 | 0.78** ± 0.02 |
| 15 | 1.42 ± 0.08 | 4.28** ± 0.37 | 0.92*† ± 0.01 | 0.89**† ± 0.04 |
| 21 | 21.7** ± 0.4 | 0.93 ± 0.03 | 0.73** ± 0.02 | 1.01 ± 0.05 |
| 16 | 1.56** ± 0.1 | 3.42** ± 0.06 | 1.08 ± 0.04 | 1.03 ± 0.04 |
| 22 | 10.5** ± 0.36 | 0.29** ± 0.03 | 0.36** ± 0.04 | 0.19** ± 0.02 |

*Values represent the average and SD of assays run in triplicate.
ND = not determined.
†Assay-to-assay variability suggests that changes of <15% in α-Tubulin are not meaningful.

Compounds 21 and 22 were found to be most active, with both compounds exhibiting a bell-shaped dose-response and inducing a profound loss of total tubulin in a dose-dependent manner. See, FIG. 1.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed is:

1. A compound of formula (I):

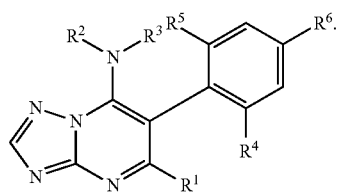

or a pharmaceutically acceptable salt or stereoisomer thereof, wherein:
$R^1$ is F, Cl, or Br;
$R^2$ is H or $C_{1-6}$ alkyl;
$R^3$ is $C_{1-6}$ alkyl, wherein the $C_{1-6}$ alkyl is substituted with one diazirinyl substituent, and further wherein the diazirinyl substituent is optionally substituted on carbon with one $R^{10}$ substituent;
$R^4$ is F, Cl, or Br;
$R^5$ is F, Cl, or Br;
$R^6$ is halogen or $C_{1-6}$ alkoxy, wherein the $C_{1-6}$ alkoxy is optionally substituted with one, two, or three substituents independently selected from the group consisting of $NR^{11}R^{12}$ and diazirinyl;
$R^{10}$ is $C_{1-6}$ alkyl or $C_{1-6}$ haloalkyl;
each $R^{11}$ is independently H or $C_{1-6}$ alkyl; and
each $R^{12}$ is independently H or $C_{1-6}$ alkyl.

2. The compound of claim 1, or a pharmaceutically acceptable salt or stereoisomer thereof, wherein $R^1$ is Cl.

3. The compound of claim 1, or a pharmaceutically acceptable salt or stereoisomer thereof, wherein $R^2$ is H.

4. The compound of claim 1, or a pharmaceutically acceptable salt or stereoisomer thereof, wherein $R^3$ is $C_{1-6}$ alkyl, wherein the $C_{1-6}$ alkyl is substituted with one diazirinyl substituent, and further wherein the diazirinyl substituent is substituted on carbon with one $R^{10}$ substituent.

5. The compound of claim 1, wherein the compound is of formula (IA):

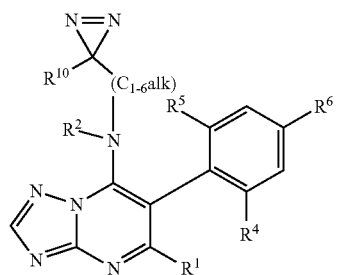

or a pharmaceutically acceptable salt or stereoisomer thereof.

6. The compound of claim 1, or a pharmaceutically acceptable salt or stereoisomer thereof, wherein:
(i) $R^4$ is F; or
(ii) $R^5$ is F; or
(iii) $R^4$ is F; and
$R^5$ is F.

7. The compound of claim 1, or a pharmaceutically acceptable salt or stereoisomer thereof, wherein $R^6$ is $C_{1-6}$ alkoxy, wherein the $C_{1-6}$ alkoxy is optionally substituted with one diazirinyl substituent.

8. The compound of claim 1, or a pharmaceutically acceptable salt or stereoisomer thereof, wherein $R^{10}$ is $C_{1-6}$ haloalkyl.

9. The compound of claim 1, or a pharmaceutically acceptable salt or stereoisomer thereof, wherein:
(i) $R^2$ is $C_{1-6}$ alkyl; or
(ii) $R^{10}$ is $C_{1-6}$ alkyl; or
(iii) $R^2$ is $C_{1-6}$ alkyl; and
$R^{10}$ is $C_{1-6}$ alkyl.

10. The compound of claim 1, wherein the compound is of formula (IB):

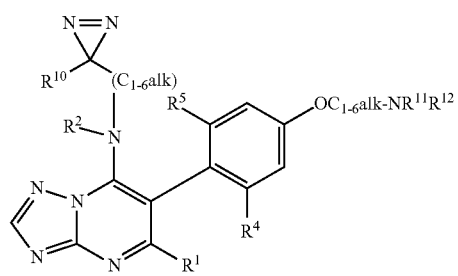

or a pharmaceutically acceptable salt or stereoisomer thereof.

11. The compound of claim 1, wherein the compound is selected from the group consisting of:

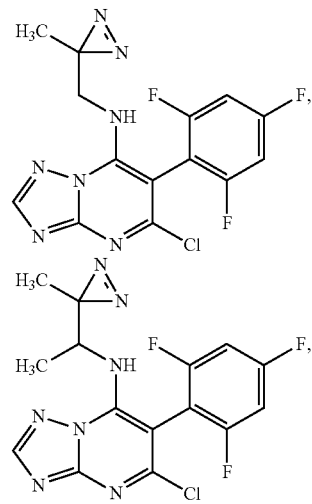

-continued

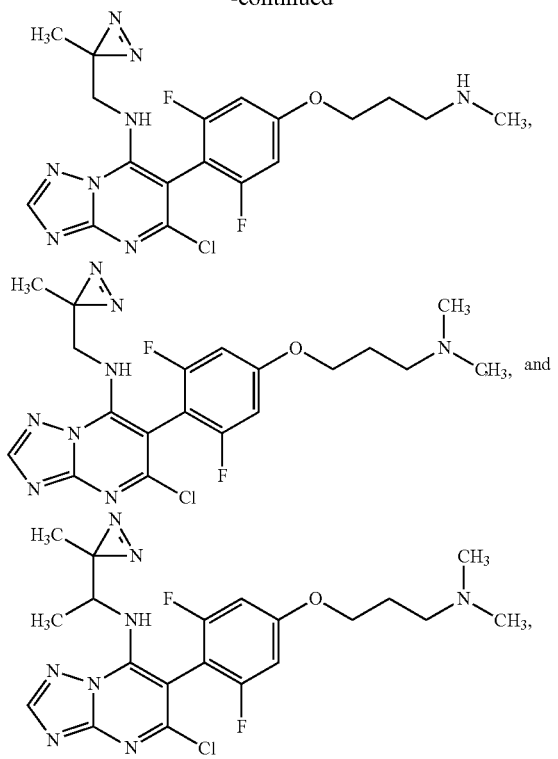

or a pharmaceutically acceptable salt or stereoisomer thereof.

12. A pharmaceutical composition comprising a pharmaceutically acceptable excipient and a compound of claim 1, or a pharmaceutically acceptable salt or stereoisomer thereof.

13. A method for stabilizing microtubules in a patient, wherein the method comprises administering to the patient in need thereof a microtubule-stabilizing amount of a compound of claim 1, or a pharmaceutically acceptable salt or stereoisomer thereof.

14. The method of claim 13, wherein the patient has cancer or a neurodegenerative disease.

15. The method of claim 14, wherein the cancer is selected from the group consisting of breast cancer, lung cancer, non-Hodgkin's lymphoma, ovarian cancer, skin cancer, and uterine cancer.

16. The method of claim 14, wherein the neurodegenerative disease is selected from the group consisting of Alzheimer's disease, amyotrophic lateral sclerosis, corticobasal degeneration, frontotemporal lobar degeneration, Lewy body disease with dementia, Parkinson's disease, Pick's disease, post-traumatic stress disorder, progressive supranuclear palsy, schizophrenia, and traumatic brain injury.

17. The method of claim 16, wherein the Parkinson's disease is Parkinson's disease with dementia.

18. The method of claim 16, wherein the traumatic brain injury is chronic traumatic encephalopathy or repetitive traumatic brain injury.

* * * * *